United States Patent
Maletic et al.

(10) Patent No.: US 9,018,200 B2
(45) Date of Patent: Apr. 28, 2015

(54) SUBSTITUTED PIPERIDINYL COMPOUNDS USEFUL AS GPR119 AGONISTS

(71) Applicant: Merck Sharp & Dohme Corp., Rahway, NJ (US)

(72) Inventors: Milana Maletic, Summit, NJ (US); Harold B. Wood, Westfield, NJ (US); Wanying Sun, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/351,723

(22) PCT Filed: Oct. 18, 2012

(86) PCT No.: PCT/US2012/060710
§ 371 (c)(1),
(2) Date: Apr. 14, 2014

(87) PCT Pub. No.: WO2013/062838
PCT Pub. Date: May 2, 2013

(65) Prior Publication Data
US 2014/0296202 A1 Oct. 2, 2014

Related U.S. Application Data

(60) Provisional application No. 61/550,627, filed on Oct. 24, 2011, provisional application No. 61/554,674, filed on Nov. 2, 2011.

(51) Int. Cl.
| | |
|---|---|
| *C07D 417/12* | (2006.01) |
| *C07D 401/12* | (2006.01) |
| *C07D 405/12* | (2006.01) |
| *C07D 211/22* | (2006.01) |
| *C07D 413/12* | (2006.01) |

(52) U.S. Cl.
CPC ............ *C07D 413/12* (2013.01); *C07D 417/12* (2013.01); *C07D 401/12* (2013.01); *C07D 405/12* (2013.01); *C07D 211/22* (2013.01)

(58) Field of Classification Search
CPC .. C07D 401/12; C07D 405/12; C07D 413/12; C07D 417/12
USPC ............ 514/210.18, 269, 316, 317, 318, 323, 514/326, 331; 544/319; 546/189, 194, 201, 546/207, 208, 209, 210, 214, 234, 239
See application file for complete search history.

(56) References Cited

U.S. PATENT DOCUMENTS

| | | | |
|---|---|---|---|
| 6,054,587 A | 4/2000 | Reddy et al. | |
| 6,110,903 A | 8/2000 | Kasibhatla et al. | |
| 6,284,748 B1 | 9/2001 | Dang et al. | |
| 6,399,782 B1 | 6/2002 | Kasibhatla et al. | |
| 6,489,476 B1 | 12/2002 | Dang et al. | |
| 6,699,871 B2 | 3/2004 | Edmondson et al. | |
| 6,730,690 B2 | 5/2004 | Olson et al. | |
| 8,343,990 B2 * | 1/2013 | Wood et al. | .................... 514/275 |
| 2009/0270409 A1 | 10/2009 | Alper et al. | |
| 2010/0022591 A1 | 1/2010 | Bertram et al. | |
| 2010/0286112 A1 | 11/2010 | Barba et al. | |
| 2011/0028501 A1 | 2/2011 | Wood et al. | |
| 2011/0212939 A1 | 9/2011 | Bartram et al. | |
| 2012/0053180 A1 | 3/2012 | Kang et al. | |
| 2012/0142706 A1 | 6/2012 | Wood et al. | |
| 2012/0196844 A1 * | 8/2012 | Alper et al. | ................ 514/210.2 |
| 2014/0256699 A1 * | 9/2014 | Miller et al. | ............... 514/210.2 |

FOREIGN PATENT DOCUMENTS

| | | |
|---|---|---|
| WO | 98/04528 A2 | 2/1998 |
| WO | 99/01423 A1 | 1/1999 |
| WO | 00/39088 A1 | 7/2000 |
| WO | 00/69810 A1 | 11/2000 |
| WO | 02/08188 A1 | 1/2002 |
| WO | 02/060388 A2 | 8/2002 |
| WO | 03/104207 A2 | 12/2003 |
| WO | 2004/019869 A2 | 3/2004 |
| WO | 2004/020408 A1 | 3/2004 |
| WO | 2004/020409 A1 | 3/2004 |
| WO | 2004/058741 A1 | 7/2004 |

(Continued)

OTHER PUBLICATIONS

Bryan et al. "Aminopyrimidine . . . " CA161:55169 (2014).*
Charette, et al., Enantioselective Cyclpropanation of Allylic Alcohols with Dioxaborolane Ligands: Scope and Synthetic Applications, vol. 120, pp. 11943-11952 (1998).
Charette, et al., Stability, Reactivity, Solution, and Solid-State Structure of Halomethylzinc Alkoxides, vol. 123, pp. 12160-12167 (2001).
Costanzi, et al., "On the applicability of GPCR Homology Models . . . ", J. Med. Chem., vol. 51, pp. 2907-2914 (2008).

(Continued)

*Primary Examiner* — Celia Chang
(74) *Attorney, Agent, or Firm* — Anna L. Cocuzzo; Catherine D. Fitch

(57) ABSTRACT

Substituted piperidinyl compounds of the formula (I): are disclosed as useful for treating or preventing type 2 diabetes and similar conditions. Pharmaceutically acceptable salts are included as well. The compounds are useful as agonists of the g-protein coupled receptor GPR-119.

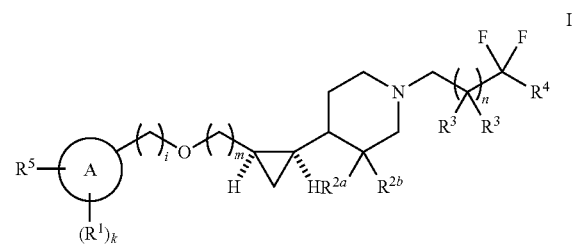

18 Claims, No Drawings

(56) References Cited

FOREIGN PATENT DOCUMENTS

| | | |
|---|---|---|
| WO | 2004/066963 A2 | 8/2004 |
| WO | 2006/067531 A1 | 6/2006 |
| WO | 2006/067532 A1 | 6/2006 |
| WO | 2007/003962 A2 | 1/2007 |
| WO | 2007/003964 A1 | 1/2007 |
| WO | 2009/011836 A1 | 1/2009 |
| WO | 2009/034388 A1 | 3/2009 |
| WO | 2009/042053 A2 | 4/2009 |
| WO | 2009/129036 A1 | 10/2009 |
| WO | 2009/000087 A1 | 12/2009 |
| WO | 2010/004343 A1 | 1/2010 |
| WO | 2010/004344 A1 | 1/2010 |
| WO | 2010/004346 A1 | 1/2010 |
| WO | 2010/004347 A1 | 1/2010 |
| WO | 2010/004348 A1 | 1/2010 |
| WO | 2010/146605 A1 | 12/2010 |
| WO | 2011/008663 A2 | 1/2011 |
| WO | 2011/019538 A1 | 2/2011 |
| WO | 2011/113947 A1 | 9/2011 |
| WO | 2011/127051 A1 | 10/2011 |
| WO | 2012/138845 A1 | 10/2012 |
| WO | 2012/173917 A1 | 12/2012 |
| WO | WO2012/170867 * | 12/2012 |
| WO | 2013/048916 A1 | 4/2013 |
| WO | 2013/074388 A1 | 5/2013 |
| WO | WO2013/062837 * | 5/2013 |
| WO | 2013/122821 A1 | 8/2013 |
| WO | 2014/025379 A1 | 4/2014 |

OTHER PUBLICATIONS

Eymery, et al., "The Usefullness of Phosphorus Compounds in Alkyne Synthesis", Synthesis, No. 2, pp. 185-213 (2000).
Lima, et al., "Bioisosterism: A Useful Strategy for Molecular Modification and Drug Design", Current Medicinal Chemistry, vol. 12, pp. 23-49 (2005).
Chaki, et al., "Recent Advances in feeding suppressing agents: potential therapeutic strategy for the treatment of obesity", Expert Opinion Ther. Patents, vol. 11, No. 11, pp. 1677-1692 (2001).
Spanswick, et al., "Emerging antiobesity drugs", Expert Opinion Emerging Drugs, vol. 8, No. 1, pp. 217-237 (2003).
Fernandez-Lopez, et al., "Pharmacological Approaches for the Treatment of Obesity", Drugs, vol. 62, No. 6, pp. 915-944 (2002).
Gadde, et al., "Combination pharmaceutical therapies for obesity", Expert Opin. Pharmacother., vol. 10, No. 6, pp. 921-925 (2009).
Szewczyk, et al., "Design of potent and selective GPR119 agonists for type II diabetes", Bioorganic & Medicinal Chemistry Letters, vol. 21, pp. 2665-2668 (2011).
International Search Report for PCT/US2012/60710, mailed Dec. 17, 2012.
Written Opinion for PCT/2012/60710, dated Nov. 30, 2012.
Supplementary European Search Report of PCT/US2012/060710, mailed Mar. 5, 2015.

* cited by examiner

SUBSTITUTED PIPERIDINYL COMPOUNDS USEFUL AS GPR119 AGONISTS

CROSS-REFERENCE TO RELATED APPLICATIONS

This application is a U.S. National Phase application under 35 U.S.C. §371 of PCT/US2012/060710, filed Oct. 18, 2012, which published as WO2013/062838 on May 2, 2013, which claims priority from U.S. provisional applications 61/554,674, filed Nov. 2, 2011, and 61/550,627, filed Oct. 24, 2011.

BACKGROUND OF THE INVENTION

The present invention relates to G-protein coupled receptor agonists. In particular, the present invention is directed to agonists of GPR 119 that are useful for the treatment of diabetes, especially type 2 diabetes, obesity, the metabolic syndrome and related diseases and conditions.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

Obesity is characterized by excessive adiposity relative to body mass. Clinically, obesity is defined by the body mass index [BMI=weight (kg)/height (m)$^2$], corresponding to BMI values ≥30. Obesity and being overweight increases the risk of developing conditions such as high blood pressure, type 2 diabetes, heart disease, stroke, osteoarthritis, sleep apnea, gallbladder disease and cancer of the breast, prostate and colon. Higher body weights are also associated with increases in all-cause mortality.

There is renewed focus on pancreatic islet-based insulin secretion that is controlled by glucose-dependent insulin secretion. In this regard, several orphan G-protein coupled receptors (GPCR's) have recently been identified that are preferentially expressed in the β-cell and are implicated in glucose dependent insulin secretion (GDIS). GPR119 is a cell-surface Gs-coupled GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. GPR119 agonists therefore have the potential to function as anti-hyperglycemic agents that produce weight loss.

WO2005/007647 published on 27 Jan. 2005, WO2005/121121 published on 22 Dec. 2005, WO2006/067531 published on 29 Jun. 2006, WO2006/067532 published on 29 Jun. 2006, WO2007003964 published on 11 Jan. 2007, and WO2007003962 published on 11 Jan. 2007 relate to GPR 119 agonist compounds.

SUMMARY OF THE INVENTION

The invention is directed to substituted piperidinyl compounds of formula I:

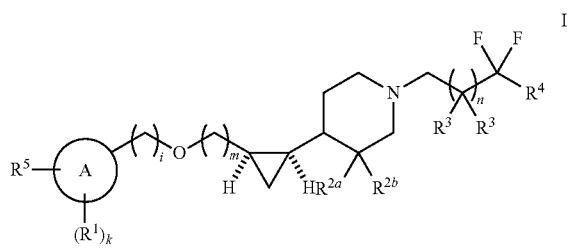

or a pharmaceutically acceptable salt thereof.

The invention further relates to methods of treating diabetes and related diseases and conditions.

DETAILED DESCRIPTION OF THE INVENTION

The invention is directed to compounds represented by formula I:

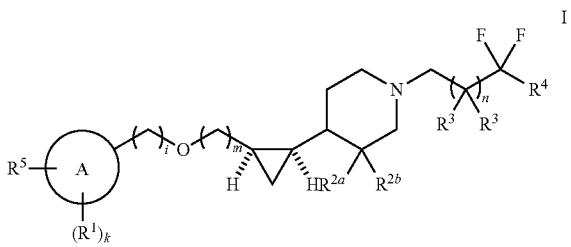

or a pharmaceutically acceptable salt thereof, wherein:
ring A is
   (1) aryl,
   (2) 9 or 10-membered fused aryl, wherein aryl is fused with a heteroaryl or heterocyclyl group,
   (3) 6-membered heteroaryl, or
   (4) 9 or 10-membered fused heteroaryl,
   wherein the heteroaryl or heterocyclyl groups contain 1-2 N atoms;
i or n are independently 0 or 1;
m is 1 or 2;
k is 0, 1, 2, or 3;
each $R^1$ is selected from the group consisting of
   (1) halo,
   (2) $C_{1-6}$alkyl,
   (3) halo$C_{1-6}$alkyl
   (4) hydroxyl,
   (5) $C_{1-6}$alkoxyl, and
   (6) amino,
   wherein the alkyl group is unsubstituted or substituted by hydroxy, $C_{1-3}$alkoxy, or halo;
$R^{2a}$ and $R^{2b}$ are independently hydrogen or halo;
each $R^3$ is independently hydrogen, halo, $C_{1-6}$alkyl, or halo$C_{1-6}$alkyl;
$R^4$ is hydrogen, halo, $C_{1-6}$alkyl, or halo$C_{1-6}$alkyl; and
$R^5$ is selected from the group consisting of
   (1) oxo,
   (2) —COOH,
   (3) —NH—C(O)$C_{1-6}$alkyl,
   (4) —C(O)$C_{1-6}$alkyl, (5) —C(O)$_2$C$_{1-6}$alkyl,
(6) —C(O)C$_{1-3}$alkyl-heteroaryl,
(7) —C(O)C$_{1-3}$alkyl-heterocyclyl,
(8) —C(O)heterocyclyl,
(9) —C(O)C$_{3-6}$cycloalkyl,
(10) —C(O)NH—C$_{1-6}$alkyl,
(11) —C(O)NH—C$_{2-6}$alkenyl,
(12) —C(O)NH—C$_{3-6}$cycloalkyl,
(13) —C(O)NH-heterocyclyl,
(14) —C(O)NH—C$_{1-3}$alkyl-C$_{3-6}$cycloalkyl,
(15) —C(O)NHC$_{1-3}$alkyl-heterocyclyl,
(16) —C(O)NHC$_{1-3}$alkyl-heteroaryl,
(17) —SO$_2$C$_{1-4}$alkyl,
(18) heteroaryl, and
(19) CN;

wherein the heteroaryl group is a 5- or 6-membered ring, containing 1-4 N, O, or S atoms; wherein the heterocyclyl group is a 3- to 6-membered ring, containing 1-2 N or O atoms; wherein the alkyl group is unsubstituted or substituted by hydroxy, C$_{1-3}$alkoxy, or halo; and wherein the cycloalkyl, heterocyclyl, or heteroaryl groups are unsubstituted or substituted with 1-3 C$_{1-6}$alkyl, halo, hydroxy, hydroxyC$_{1-6}$alkyl, or C$_{1-6}$alkoxyl groups.

In one embodiment, the invention is directed to compounds of formula I or a pharmaceutically acceptable salt, wherein ring A is aryl, 9 or 10-membered fused aryl, wherein aryl is fused with a heteroaryl or heterocyclyl group, 6-membered heteroaryl, or 9 or 10-membered fused heteroaryl, wherein the heteroaryl or heterocyclyl groups contain 1-2 N atoms.

In one class of this embodiment, ring A is aryl, 9 or 10-membered fused aryl, wherein aryl is fused with a heteroaryl or heterocyclyl group, or heteroaryl. In a class of this embodiment, ring A is an aryl. In another class of this embodiment, ring A is a 9 or 10-membered fused aryl, wherein aryl is fused with a heteroaryl or heterocyclyl group. In another class of this embodiment, ring A is a 9 or 10-membered fused aryl, wherein aryl is fused with a heterocyclyl group.

In another class of this embodiment, ring A is a 6-membered heteroaryl containing 1-2 N atoms. In yet another class of this embodiment, ring A is a 9 or 10-membered fused heteroaryl containing 1-2 N atoms.

In one class of this embodiment, ring A is phenyl, 2,3-dihydro-indolyl, pyridinyl, or pyrimidinyl. On class of this embodiment, ring A is phenyl. In another class of this embodiment, ring A is 2,3-dihydro-indoyl. In another class of this embodiment, ring A is pyridinyl. In another class of this embodiment, ring A is pyrimidinyl.

In one embodiment, the invention is directed to compounds of formula I or a pharmaceutically acceptable sat, wherein R is selected from the group consisting of —COOH, —NH—C(O)C$_{1-6}$alkyl, —C(O)C$_{1-6}$alkyl, —C(O)$_2$C$_{1-6}$alkyl, —C(O)C$_{1-3}$alkyl-heteroaryl, —C(O)C$_{1-3}$alkyl-heterocyclyl, —C(O)heterocyclyl, —C(O)C$_{3-6}$cycloalkyl, —C(O)NH—C$_{1-6}$alkyl, —C(O)NH—C$_{2-6}$alkenyl, —C(O)NH—C$_{3-6}$cycloalkyl, —C(O)NH-heterocyclyl, —C(O)NH—C$_{1-3}$alkyl-C$_{3-6}$cycloalkyl, —C(O)NHC$_{1-3}$alkyl-heterocyclyl, —C(O)NHC$_{1-3}$alkyl-heteroaryl, —SO$_2$C$_{1-4}$alkyl, heteroaryl, and CN;

wherein the heteroaryl group is a 5- or 6-membered ring, containing 1-4 N, O, or S atoms; wherein the heterocyclyl group is a 3- to 6-membered ring, containing 1-2 N or O atoms; wherein the alkyl group is unsubstituted or substituted by hydroxy, C$_{1-3}$alkoxy, or halo; and wherein the cycloalkyl, heterocyclyl, or heteroaryl groups are unsubstituted or substituted with 1-3 C$_{1-6}$alkyl, halo, hydroxy, hydroxyC$_{1-6}$alkyl, or C$_{1-6}$alkoxyl groups.

In a class of this embodiment, the heteroaryl group is a 5-membered ring, containing 1-4 N, O, or S atoms.

In one class of this embodiment, R$^5$ is selected from the group consisting of oxo, —COOH, —C(O)C$_{1-6}$alkyl, —C(O)$_2$C$_{1-6}$alkyl, —C(O)C$_{1-3}$alkyl-heteroaryl, —C(O)C$_{1-3}$alkyl-heterocyclyl, —C(O)heterocyclyl, —C(O)C$_{3-6}$cycloalkyl, —C(O)NHC$_{1-6}$alkyl, —C(O)NHC$_{2-6}$alkenyl, —C(O)NHC$_{3-6}$cycloalkyl, —C(O)NH-heterocyclyl, —C(O)NHC$_{1-3}$alkyl-heterocyclyl, —C(O)NHC$_{1-3}$alkyl-heteroaryl, —C(O)NHC$_{1-3}$alkyl-C$_{3-6}$cycloalkyl, —SO$_2$C$_{1-4}$alkyl, heteroaryl, and CN;

wherein the heteroaryl group is a 5- or 6-membered ring, containing 1-4 N, O, or S atoms; wherein the heterocyclyl group is a 3- to 6-membered ring, containing 1-2 N or O atoms; wherein the alkyl group is unsubstituted or substituted by hydroxy, C$_{1-3}$alkoxy, or halo; and wherein the cycloalkyl, heterocyclyl, or heteroaryl groups are unsubstituted or substituted with 1-3 C$_{1-6}$alkyl, halo, hydroxy, hydroxyC$_{1-6}$alkyl, or C$_{1-6}$alkoxyl groups.

In a subclass of this class, the heteroaryl group is a 5-membered ring, containing 1-4 N, O, or S atoms.

In one class of this embodiment, R$^5$ is selected from the group consisting of oxo, —COOH, —C(O)C$_{1-6}$alkyl, —C(O)$_2$C$_{1-6}$alkyl, —C(O)heterocyclyl, —C(O)NHC$_{1-6}$alkyl, —C(O)NHC$_{3-6}$cycloalkyl, —C(O)NHheterocyclyl, —C(O)NHC$_{1-3}$alkyl-heterocyclyl, —C(O)NHC$_{1-3}$alkyl-heteroaryl, —C(O)NHC$_{1-3}$alkyl-C$_{3-6}$cycloalkyl, —SO$_2$C$_{1-4}$alkyl, and CN;

wherein the heteroaryl group is a 5- or 6-membered ring, containing 1-4 N, O, or S atoms; wherein the heterocyclyl group is a 3- to 6-membered ring, containing 1-2 N or O atoms; wherein the alkyl group is unsubstituted or substituted by hydroxy, C$_{1-3}$alkoxy, or halo; and wherein the cycloalkyl, heterocyclyl, or heteroaryl groups are unsubstituted or substituted with 1-3 C$_{1-6}$alkyl, halo, hydroxy, hydroxyC$_{1-6}$alkyl, or C$_{1-6}$alkoxyl groups.

In a subclass of this class, the heteroaryl group is a 5-membered ring, containing 1-4 N, O, or S atoms.

In one class of this embodiment, R$^5$ is selected from the group consisting of oxo, cyano,

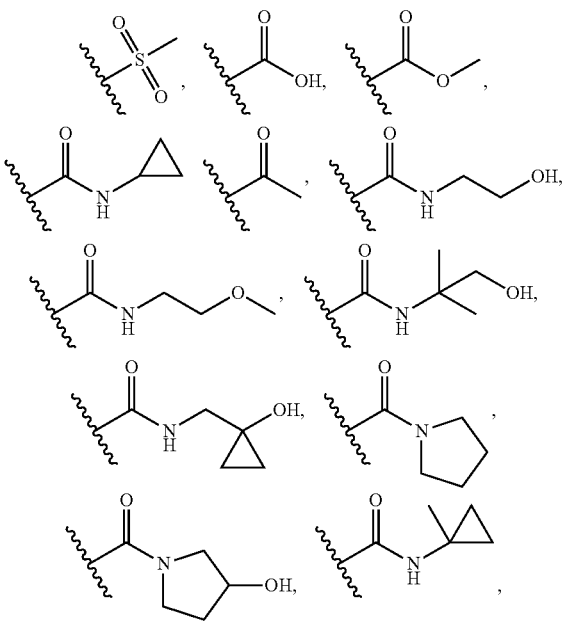

-continued

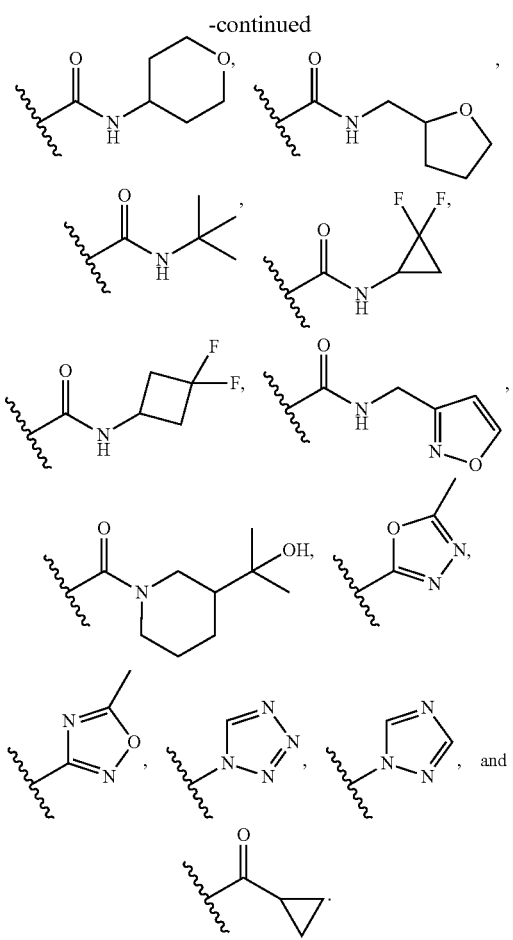

In one embodiment, the invention is directed to compounds of formula I or a pharmaceutically acceptable salt, wherein each $R^1$ is selected from the group consisting of halo, $C_{1-6}$alkyl, halo$C_{1-6}$alkyl, hydroxyl, $C_{1-6}$alkoxyl, and amino, wherein the alkyl group is unsubstituted or substituted by hydroxy, $C_{1-3}$alkoxy, or halo.

In one class of this embodiment, $R^1$ is selected from the group consisting of fluoro, and methyl.

In one embodiment, the invention is directed to compounds of formula I or a pharmaceutically acceptable salt, wherein $R^{2a}$ and $R^{2b}$ are hydrogen or halo. In one class of this embodiment, $R^{2a}$ and $R^{2b}$ are hydrogen. In one class of this embodiment, $R^{2a}$ and $R^{2b}$ are halo. In another class of this embodiment, $R^{2a}$ is halo, and $R^{2b}$ is hydrogen. In another class of this embodiment, $R^{2a}$ is fluoro, and $R^{2b}$ is hydrogen.

In one embodiment, the invention is directed to compounds of formula I or a pharmaceutically acceptable salt, wherein each $R^3$ is independently hydrogen, halo, $C_{1-6}$alkyl, or halo$C_{1-6}$alkyl. In one class of this embodiment, each $R^3$ is independently hydrogen, fluoro or methyl. In one class of this embodiment, each $R^3$ is independently fluoro. In one class of this embodiment, each $R^3$ is independently hydrogen. In one class of this embodiment, each $R^3$ is independently methyl.

In one embodiment, the invention is directed to compounds of formula I or a pharmaceutically acceptable salt, wherein $R^4$ is hydrogen, halo, $C_{1-6}$alkyl, or halo$C_{1-6}$alkyl.

In one class of this embodiment, $R^4$ is hydrogen.

In one class of this embodiment, $R^4$ is $C_{1-6}$alkyl. In a subclass of this class, $R^4$ is methyl or ethyl.

In another class of this embodiment, $R^4$ is halo. In a subclass of this class, $R^4$ is fluoro.

In one class of this embodiment, $R^4$ is halo$C_{1-6}$alkyl. In a subclass of this class, $R^4$ is difluoromethyl or trifluoromethyl.

In one class of this embodiment, $R^4$ is fluoro, methyl, ethyl, difluoromethyl, or trifluoromethyl.

In one embodiment, the invention is directed to compounds of formula I or a pharmaceutically acceptable salt, wherein i is 0, or 1; and m is 1 or 2, such that the sum of i and m is 2.

In another embodiment, the invention is directed to compounds of formula I or a pharmaceutically acceptable salt, wherein i is 0; and m is 1 or 2. In a class of this embodiment, m is 1. In another class of this embodiment, m is 2.

In another embodiment, the invention is directed to compounds of formula I or a pharmaceutically acceptable salt, wherein i is 1; and m is 1 or 2. In a class of this embodiment, i is 1; and m is 1. In another class of this embodiment, i is 1; and m is 2.

In one embodiment, the invention is directed to compounds of formula I or a pharmaceutically acceptable salt, wherein:
ring A is phenyl, 2,3-dihydro-indolyl, pyridinyl, or pyrimidinyl; and
$R^5$ is selected from the group consisting of oxo, cyano,

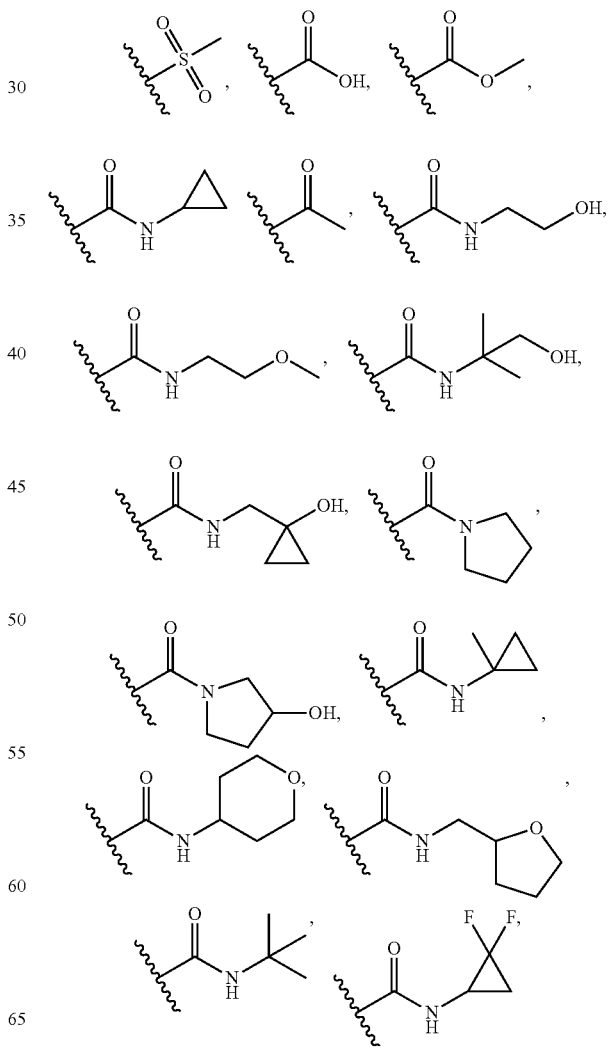

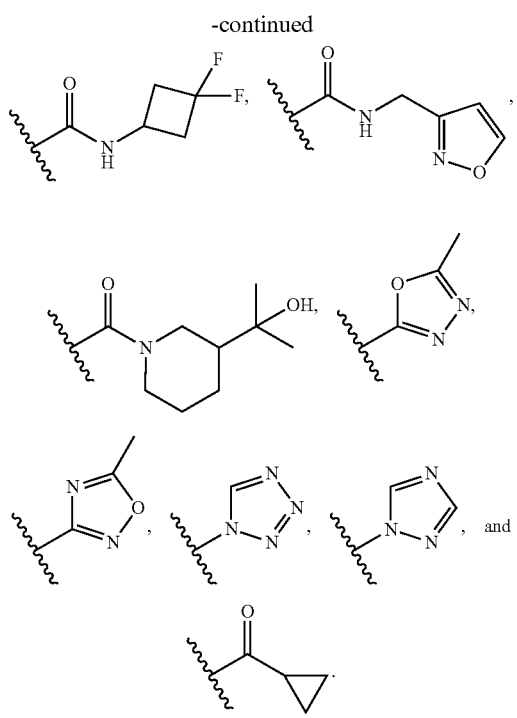

In a class of this embodiment, ring A is phenyl.

In a subclass of this class, each $R^1$ is selected from the group consisting of fluoro, and methyl; and $R^{2a}$ and $R^{2b}$ are hydrogen.

In another class of this embodiment, ring A is 2,3-dihydroindolyl.

In a subclass of this class, each R' is selected from the group consisting of fluoro, and methyl; and $R^{2a}$ and $R^{2b}$ are hydrogen.

In another class of this embodiment, ring A is pyridinyl.

In a subclass of this class, each $R^1$ is selected from the group consisting of fluoro, and methyl; and $R^{2a}$ and $R^{2b}$ are hydrogen.

In yet another class of this embodiment, ring A is pyrimidinyl.

In a subclass of this class, each $R^1$ is selected from the group consisting of fluoro, and methyl; and $R^{2a}$ and $R^{2b}$ are hydrogen.

In one embodiment, the invention is directed to a compound represented by formula I-A:

I-A

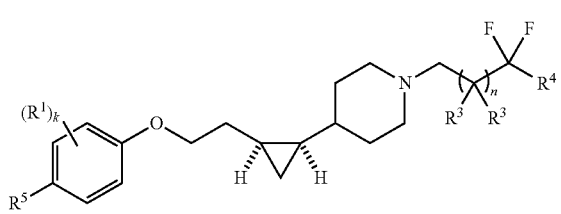

or a pharmaceutically acceptable salt thereof, wherein $R^1$, $R^3$, $R^4$, $R^5$, k, and n are as previously defined.

In one embodiment, the invention is directed to a compound represented by formula I-B:

I-B

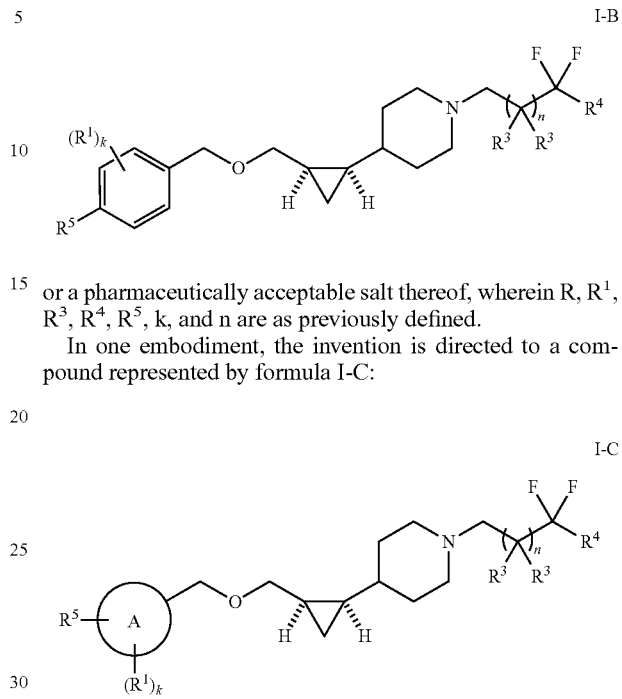

or a pharmaceutically acceptable salt thereof, wherein R, $R^1$, $R^3$, $R^4$, $R^5$, k, and n are as previously defined.

In one embodiment, the invention is directed to a compound represented by formula I-C:

I-C or a pharmaceutically acceptable salt thereof, wherein $R^1$, $R^3$, $R^4$, $R^5$, k, and n are as previously defined, and ring A is selected from the group consisting of pyridinyl or pyrimidinyl.

In one class of this embodiment, ring A is pyridinyl. In another class of ring A is pyrimidinyl.

In one embodiment, the invention is directed to a compound represented by formula I-D:

I-D

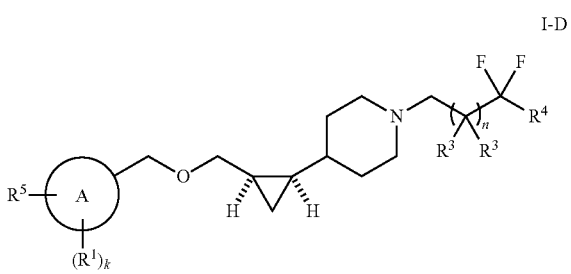

or a pharmaceutically acceptable salt thereof, wherein $R^1$, $R^3$, $R^4$, $R^5$, k, and n are as previously defined, and ring A is selected from the group consisting of pyridinyl or pyrimidinyl.

In one class of this embodiment, ring A is pyridinyl. In another class of ring A is pyrimidinyl.

The invention is described herein in detail using the terms defined below unless otherwise specified.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkenyl," means carbon chains which may be linear or branched, or combinations thereof, containing indicated number of carbon atoms that contain one or more double bonds. The double bonds may be conjugated or nonconjugated. Examples of alkenyl groups include ethane, propene, 2-methylprop-1-ene, or penta-1,3-diene, and the like.

As used herein, "cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkoxy" refers to an alkyl group linked to oxygen.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Haloalkoxy" and "haloalkylO" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Haloalkyl" include mono-substituted as well as multiple halo substituted alkyl groups, up to perhalo substituted alkyl. For example, trifluoromethyl is included.

"Heteroaryl" (HAR) unless otherwise specified, means an aromatic or partially aromatic ring system that contains at least one ring heteroatom selected from O, S and N. Heteroaryls thus includes heteroaryls fused to other kinds of rings, such as aryls, cycloalkyls and heterocyclyls that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 3-15 atoms are included, forming 1-3 rings.

"Heterocyclyl" unless otherwise specified, means a non-aromatic ring system containing 3-8 atoms that contains at least one ring heteroatom selected from O, S and N. Examples of heterocyclyl groups include: piperidine, piperazine, morpholine, pyrrolidine, tetrahydrofuran, azetidine, oxirane, or aziridine, and the like.

"Halogen" (Halo) includes fluorine, chlorine, bromine and iodine.

"Thioalkoxy" means alkoxy group whereby the oxygen group is replaced by sulfur.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of Formula I and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Compounds of the present invention are potent agonists of the GPR 119 receptor. These compounds and pharmaceutically acceptable salts thereof are modulators of the receptor known as GPR 119, and are therefore useful in the treatment of diseases that are modulated by GPR119 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) Hyperapobetalipoproteinemia; and
(11) atherosclerosis.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

Additionally, by keeping hyperglycemia under control, the compounds are useful to delay or for preventing vascular restenosis and diabetic retinopathy.

The compounds of this invention are useful in improving or restoring 0-cell function, so that they may be useful in treating type 1 diabetes or in delaying or preventing a patient with type 2 diabetes from needing insulin therapy.

The compounds, compositions, and medicaments as described herein are further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

In one embodiment, the invention provides a method for the treatment of a condition selected from the group consisting of diabetes and obesity comprising administering to an individual a pharmaceutical composition comprising the compound of formula I.

In one embodiment, the invention provides a compound according to formula I for use as a medicament.

In one embodiment, the invention provides a compound according to formula I for use in the treatment of diabetes or obesity. In one class, the invention provides a compound according to formula I for use in the treatment of diabetes. In one class, the invention provides a compound according to formula I for use in the treatment of obesity.

In one embodiment, the invention provides a use of a compound of formula I, or a pharmaceutically acceptable salt thereof, in the manufacture of a medicament for use in treating a condition selected from the group consisting of diabetes and obesity.

One embodiment of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another embodiment of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat,) or a monoamine neurotransmitter uptake inhibitor (e.g., sibutramine or phentermine). The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another embodiment of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another embodiment of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another embodiment of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another embodiment of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists;
(h) GIP, GIP mimetics, and GIP receptor agonists;
(i) PACAP, PACAP mimetics, and PACAP receptor δ agonists;
(j) cholesterol lowering agents selected from the group consisting of
(i) HMG-CoA reductase inhibitors, (ii) sequestrants, (iii) nicotinyl alcohol, nicotinic acid and salts thereof, (iv) PPARα agonists, (v) PPAR α/γ dual agonists, (vi) inhibitors of cholesterol absorption, (vii) acyl CoA:cholesterol acyltransferase inhibitors, and (viii) anti-oxidants;
(k) PPARδ agonists;
(l) SGLT inhibitors (e.g., dapagliflozin, canagliflozin, BI-10773, PF-729, tofogliflozin, ipragliflozin, LX-4211);
(m) antiobesity compounds;
(n) ileal bile acid transporter inhibitors;
(o) anti-inflammatory agents excluding glucocorticoids;
(p) protein tyrosine phosphatase-1B (PTP-1B) inhibitors; and
(q) antihypertensives including those acting on the angiotensin or renin systems, such as angiotensin converting enzyme inhibitors, angiotensin II receptor antagonists or renin inhibitors, (e.g., lisinopril, losartan); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another embodiment of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

As discussed supra, compounds of the present invention may be used in combination with other drugs that may also be useful in the treatment or amelioration of the diseases and conditions described herein. Such other drugs may be administered by a route and in an amount commonly used therefore, contemporaneously or sequentially with a compound of the formulas described herein or a pharmaceutically acceptable salt thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of the formulas described herein is used contemporaneously with one or more other drugs, a pharmaceutical composition in unit dosage form containing such other drugs and the compound of the formulas described herein is preferred. However, the combination therapy also includes therapies in which a compound of the formulas described herein and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered separately or in the same pharmaceutical composition in combination with a compound of the formulas described herein include, but are not limited to:

(1) dipeptidyl peptidase-IV (DPP-4) inhibitors;
(2) insulin sensitizers, including
  (i) PPARγ agonists, such as the glitazones (e.g. pioglitazone), and other PPAR ligands, including (1) PPARα/γ. dual agonists (e.g., muraglitazar,); (2) PPARα agonists, such as fenofibric acid derivatives (e.g., gemfibrozil), (3) selective PPARγ modulators (SPPARγM's); and (4) PPARγ. partial agonists;
  (ii) biguanides, such as metformin and its pharmaceutically acceptable salts, in particular, metformin hydrochloride, and extended-release formulations thereof, such as Glumetza™, Fortamet™, and GlucophageXR™; and
  (iii) protein tyrosine phosphatase-1B (PTP-1B) inhibitors;
(3) insulin or insulin analogs;
(4) leptin and leptin derivatives and agonists;
(5) amylin and amylin analogs, such as pramlintide;
(6) sulfonylurea and non-sulfonylurea insulin secretagogues;
(7) α-glucosidase inhibitors (e.g., acarbose);
(8) glucagon receptor antagonists;
(9) incretin mimetics, such as GLP-1, GLP-1 analogs, derivatives, and mimetics; and GLP-1 receptor agonists;
(10) LDL cholesterol lowering agents such as (i) HMG-CoA reductase inhibitors (e.g., simvastatin), (ii) bile acid sequestering agents (e.g., cholestyramine), (iii) inhibitors of cholesterol absorption, (e.g., ezetimibe), and (iv) acyl CoA:cholesterol acyltransferase inhibitors, (e.g., avasimibe);
(11) HDL-raising drugs, (e.g., niacin and nicotinic acid receptor agonists);
(12) antiobesity compounds;
(13) agents intended for use in inflammatory conditions, such as aspirin, non-steroidal anti-inflammatory drugs or NSAIDs, glucocorticoids, and selective cyclooxygenase-2 or COX-2 inhibitors;
(14) antihypertensive agents, such as ACE inhibitors (e.g., lisinopril), A-II receptor blockers (e.g., losartan), renin inhibitors (e.g., aliskiren), beta blockers, and calcium channel blockers;
(15) glucokinase activators (GKAs);
(16) inhibitors of 11β-hydroxysteroid dehydrogenase type 1, (e.g., those disclosed in U.S. Pat. No. 6,730,690);
(17) CETP inhibitors (e.g., anacetrapib);
(18) inhibitors of fructose 1,6-bisphosphatase, (e.g., those disclosed in U.S. Pat. No. 6,054,587);
(19) inhibitors of acetyl CoA carboxylase-1 or 2;
(20) AMP-activated Protein Kinase (AMPK) activators;
(21) other agonists of the G-protein-coupled receptors: GPR-109, GPR-119, and GPR-40;
(22) SSTR3 antagonists;
(23) neuromedin U receptor agonists;
(24) SCD inhibitors;
(25) GPR-105 antagonists;
(26) SGLT inhibitors (e.g., dapagliflozin, canagliflozin, BI-10773, PF-729, tofogliflozin, ipragliflozin, LX-4211);
(27) inhibitors of acyl coenzyme A:diacylglycerol acyltransferase 1 and 2 (DGAT-1 and DGAT-2);
(28) inhibitors of fatty acid synthase;
(29) inhibitors of acetyl-CoA carboxylase-1 and 2 (ACC-1 and ACC-2);
(30) inhibitors of acyl coenzyme A:monoacylglycerol acyltransferase 1 and 2 (MGAT-1 and MGAT-2);
(31) agonists of the TGR5 receptor (also known as GPBAR1, BG37, GPCR19, GPR131, and M-BAR);
(32) ileal bile acid transporter inhibitors;
(33) PACAP, PACAP mimetics, and PACAP receptor δ agonists;
(34) PPAR agonists;
(35) protein tyrosine phosphatase-1B (PTP-1B) inhibitors; and
(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), MK-3102, SYR-472, teneligliptin, KRP104, TS021, AMG222, SK0403, LC15-0444, vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:
(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;
(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;
(2R,3S,5R)-2-(2,5-difluorophenyl)tetrahydro)-5-(4,6-dihydropyrrolo[3,4-c]pyrazol-5(1H)-yl)tetrahydro-2H-pyran-3-amine;
(3R)-4-[(3R)-3-amino-4-(2,4,5-trifluorophenyl)butanoyl]-hexahydro-3-methyl-2H-1,4-diazepin-2-one;
4-[(3R)-3-amino-4-(2,5-difluorophenyl)butanoyl]hexahydro-1-methyl-2H-1,4-diazepin-2-one hydrochloride; and
(3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Another embodiment of the invention that is of interest relates to the use of a compound in accordance with the formulas described herein or a pharmaceutically acceptable salt thereof in the manufacture of a medicament for use in treating a disease or condition described herein.

The compounds of the invention can be prepared using the synthetic schemes described herein as well as any of several alternate methods which will be apparent to a chemist skilled in the art.

The following abbreviations may be used in the synthetic schemes or Examples: AcCN is acetonitrile; Boc is t-butyloxycarbonyl; Cbz is benzyloxycarbony; DBAD is dibenzyl azodicarboxylate; DCM is dichloromethane; DEAD is diethyl azodicarboxylate; DIPEA (DIEA) is N,N-Diisopropylethylamine, or Hünig's base; DMF is N,N-dimethylformamide; EDC is 1-ethyl-3-[3-(dimethylamino)propyl]-carbodiimide HCl; eq. is equivalent; EtOAc is ethyl acetate; EtOH is ethanol; g is gram; HCl is hydrochloric acid; HOBt is 1-hydroxybenzotriazole; HPLC is high performance liquid chromatography; L is liter; LAH is lithium aluminum hydride; LCMS is liquid chromatography mass spectrometry; LRMS is low resolution mass spectrometry; M is molar; mg is milligram; min. is minute; mmol is millimole; MeOH is methanol; n-BuLi is n-butyllithium; nM is nanomolar; RPHPLC is reverse phase high performance liquid chromatography; RT is room temperature; TBDMS is t-butyldimethylsilyl; TBAF is tetrabuthyl ammonium fluoride; TEA is triethylamine; Tf is triflate; TFA is trifluoroacetic acid; THF is tetrahydrofuran; TLC is thin layer chromatography; TPAP is tetrapropylammonium perruthenate.

Reaction Schemes below illustrate the methods employed in the synthesis of the compounds of the present invention of Formula I. All substituents are as defined above unless indicated otherwise. The synthesis of the novel compounds of the present invention may be accomplished by one or more of synthetic scheme.

General Schemes

The intermediates shown in the schemes are commercially available or may be prepared from readily accessible starting materials via a host of routes.

The cyclopropyl residue in the connecting chain of the present examples may be introduced by any of several methods. A particularly convenient method is outlined in Scheme 1 below. Conversion of the readily available hydroxymethyl piperidine to the acetylene by a multistep protocol allows ready access to the indicated cis olefins after Lindlar reduction. (see, e.g., Eymery, et al, *Synth* 2000, 185-213 at page 196 for a convenient protocol). Charette's $Et_2Zn/CH_2I_2$ cyclopropanation affords racemic, diasteromerically enriched or enantiomerically enriched cyclopropyl analogs. (Charette et al, *JACS* 1998, 120, 11943-11952; further details in Charette, et al, *JACS*, 2001, 123, 12160-12167.) In the absence of an auxiliary chiral Lewis acid the cis allylic olefin affords good yields of the desired racemic analog. Also in the absence of an auxiliary chiral Lewis acid, the chiral alcohol derived from the opening of R or S glycidyl epoxide affords reasonable ratios the chiral diasteromeric cyclopropanation products.

With the addition of the auxiliary chiral Lewis acid RR or SS BuTMDOB, the same cyclopropanation protocol leads to very good ratios of the desired enantiomer in either the allylic or homoallylic cyclopropanation. The depicted chiral homoallylic alcohol requires the "matched" dioxaborolane in the double diasteroselection protocol.

Scheme 1:

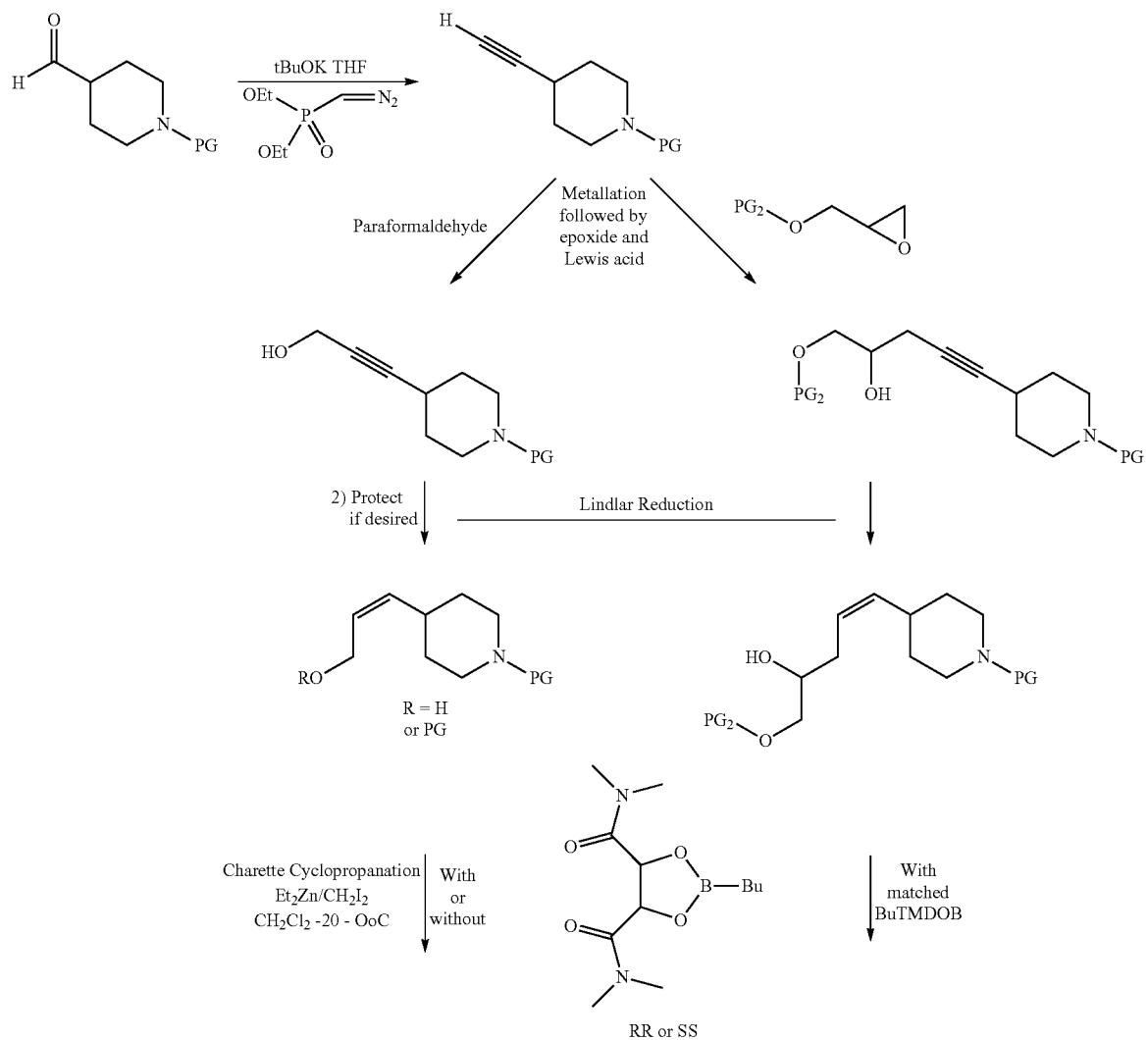

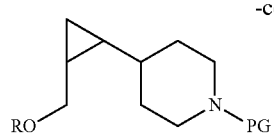
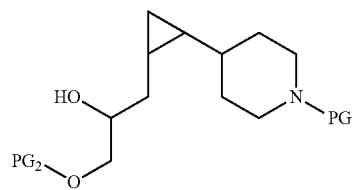

1) Deprotect if required
2) TPAP NMO
3) Ph₃PCH₂OMe Base
4) H⁺
5) NaBH₄

1) Deprotection
2) NaIO₄
3) NaBH₄

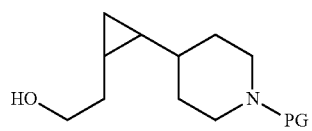

R' represents lower alkyl, PG2 represents a protecting group, preferably benzyl

The compounds of the cyclopropyl series can be synthesized using the method outlined in Scheme 2-A below. Conversion of the readily available CBZ protected piperidine to the amine is accomplished by hydrogenation over palladium on carbon. The amine selectively displaces the triflate to yield the substituted amine. The final compound can be synthesized using Mitsunobu conditions or by synthesizing the alkoxide and displacing a halo compound.

Scheme 2-A: General Synthetic Scheme for the Cycloalkyl Series

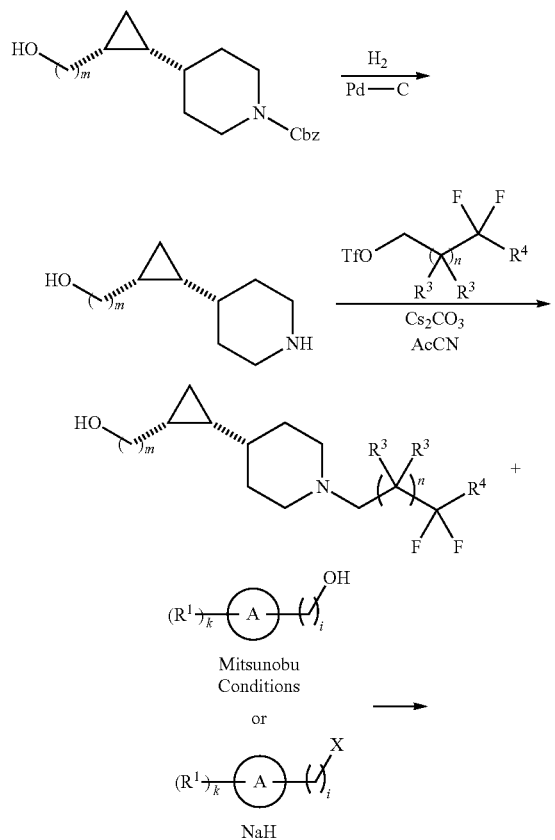

-continued

Alternatively, the compounds of the cyclopropyl series can be synthesized by using the method outlined in Scheme 2-B below. Starting from the Cbz protected piperidine, the ether can be synthesized using Mitsunobu conditions. Following, the piperidine is deprotected to give the amine. Then, the peptide coupling using a reagent such as EDC/HOBt/DIEA affords the amide compound. The final compound can be obtained by reducing the carbonyl using lithium aluminum hydride.

Scheme 2-B: Alternative Synthetic Scheme for the Cycloalkyl Series

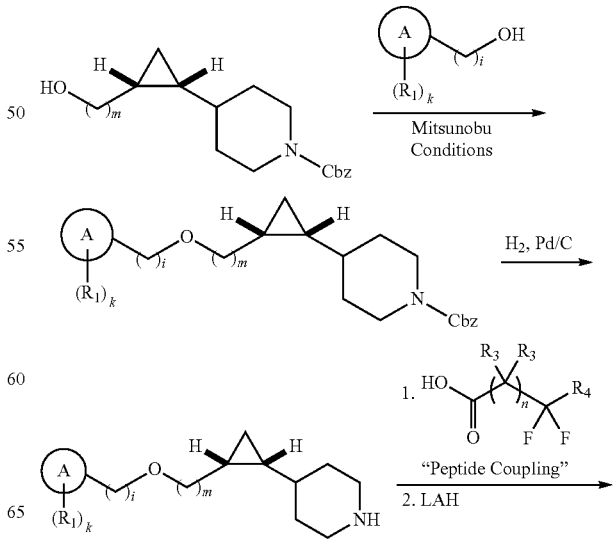

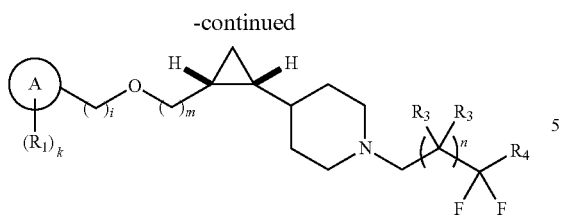

The compounds of the cyclopropyl series can be obtained according to Scheme 2-C by first protecting the alcohol with the TBDMS group, followed by the selective deprotection of the amine group by reaction with hydrogen gas over Pd/C. The amine is reacted by an activated carboxylic acid under standard peptide coupling conditions followed by LAH reduction. The TBDMS group can be selectively removed using TBAF to give the alcohol. The final compound is obtained by reaction with another alcohol under Mitsunobu conditions.

Scheme 2-C: Alternative Synthetic Scheme for the Cycloalkyl Series

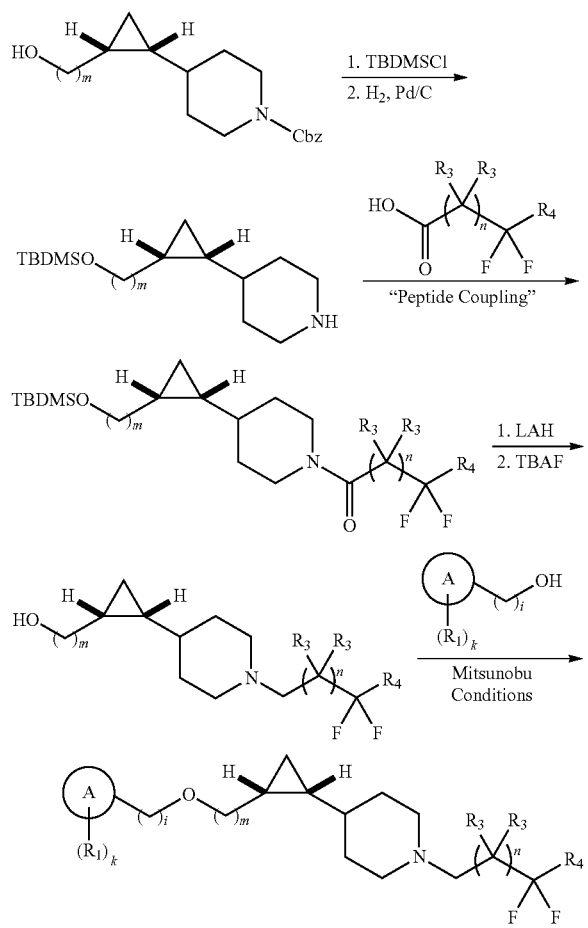

Many examples are prepared as the racemic mixture and separated by chromatography on chiral stationary phase. Several commercially available stationary phases are suitable for this purpose. Comercial Chiralpak IA 4.6×250 mm, 5μ columns are typically used for analytical work and semi-prep Chiralpak IA columns (20×250 mm, 5μ) for preparative separations. Heptane alcohol mixtures are typically used to elute the enantiomers.

Intermediates

Intermediate 1

2-[(1S,2R)-2-(piperidin-4-yl)cyclopropyl]ethanol

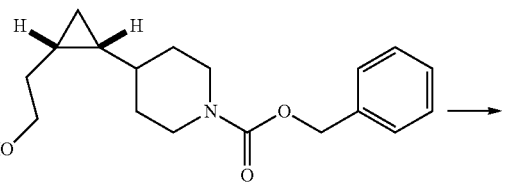

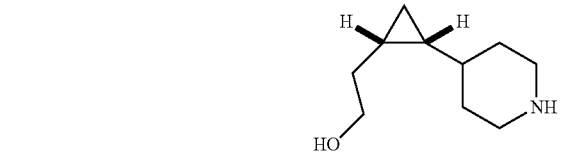

A solution of 4-[(1R,2S)-2-(2-hydroxyethyl)cyclopropyl]piperidine-1-carboxylate (2.3 g, 7.58 mmol) in 10 mL of MeOH and 10 mL of EtOAc was added Pd—C (10%) (500 mg) followed by hydrogenation with balloon at room temperature for 1 hr. The solid was removed by filtration. The solvent was removed under vacuum to yield Intermediate 1. LCMS calc: 169.26; obs: 170.28 (M+1)

Intermediate 2

2-((1S,2R)-2-[1-(2,2,2-trifluoroethyl)piperidin-4-yl]cyclopropyl)ethanol

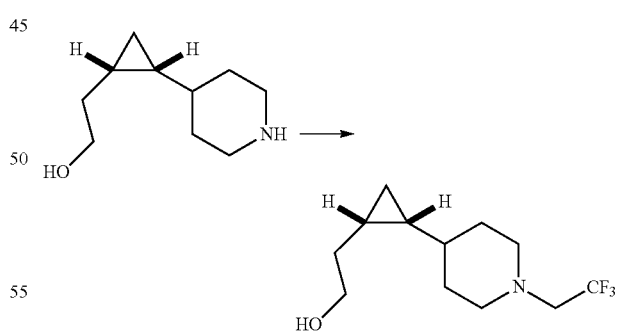

To a solution of 2-[(1S,2R)-2-(piperidin-4-yl)cyclopropyl]ethanol (100 mg, 0.59 mmol) in 3.0 mL acetonitrile was added cesium carbonate (230 mg, 0.71 mmol) followed by addition of 2,2,2-trifluoroethyl trifluoromethanesulfonate (165 mg, 0.71 mmol). The reaction mixture was stirred at room temperature for 3 hours. It was diluted with 10 mL of EtOAc, washed with water, brine, dried over sodium sulfate, filtered and stripped to give Intermediate 2. LCMS calc: 251.29; obs: 252.13 (M+1)

Using a similar synthetic procedure the following compounds were synthesized

| Intermediates | Compound | Observed Mass (M + H) |
|---|---|---|
| Int-3 | | 248.13 |
| Int-4 | | 302.04 |
| Int-5 | | 284.11 |
| Int-6 | | 266.23 |
| Int-7 | | 294.16 |
| Int-8 | | 262.19 |

Intermediate 9 tert-Butyl 4-[(1S,2R)-2-(hydroxymethyl)cyclopropyl]piperidine-1-carboxylate

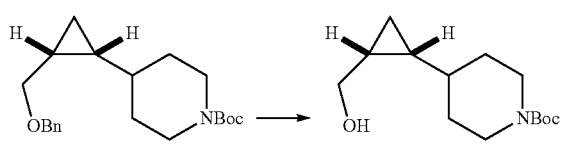 [SMILES: CC(C)(C)OC(=O)N1CCC([C@H]2C[C@H]2COCc2ccccc2)CC1 ; CC(C)(C)OC(=O)N1CCC([C@H]2C[C@H]2CO)CC1]

The benzyl protected hydroxyethylcyclopropane from step 4 of this example (6 g, 1 eq.) was dissolved in a mixture of HPLC grade EtOAc (75 mL) and ethanol (75 mL). The solution was degassed and backfilled with nitrogen, before Pd(OH)$_2$ (20 w % on carbon, 2.34 g, 0.2 eq.) was added. The reaction vessel was degassed and backfill with hydrogen three times. The reaction mixture was rigorously stirred under a 1 L hydrogen balloon and was monitored by LC-MS. The deprotection is typically complete within 2 hours. The mixture was then filtered through a plug of silica gel (100 g) and was washed thoroughly with 50% EtOAc/hexanes (1 L). Concentration gave the Intermediate 9 as colorless oil.

Intermediate 10

[(1R,2R)-2-(piperidin-4-yl)cyclopropyl]methanol

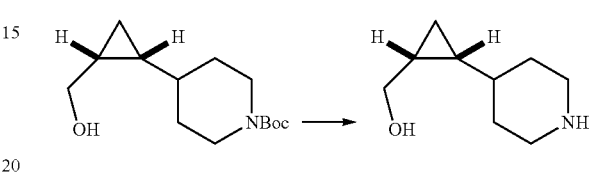

To a solution of tert-butyl-4-[(1R,2R-2-(hydroxymethyl)cyclopropyl)piperidine-1-carboxylate (11.8 g, 46.2 mmol) in DCM (300 ml) was added TFA (178 ml, 2311 mmol) at RT. The solution was stirred at RT for 30 min. The solvent was removed under vacuum to give Intermediate 10.

EXAMPLES

Example 1

Methyl 2,6-difluoro-4-(2-{(1S,2R)-2-[1-(2,2,2-trifluoroethyl)piperidin-4-yl]cyclopropyl}ethoxy)benzoate

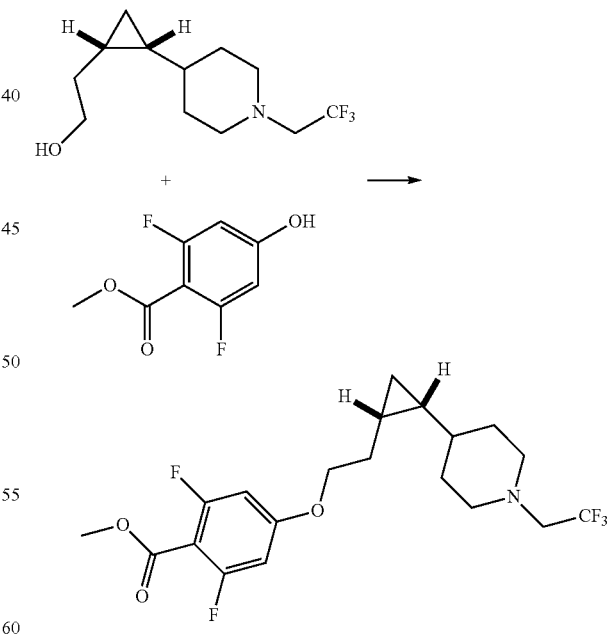

-((1S,2R)-2-[1-(2,2,2-trifluoroethyl)piperidin-4-yl]cyclopropyl)ethanol (40 mg, 0.159 mmol), polymer-supported triphenylphosphine (158 mg, 0.478 mmol) and methyl 2,6-difluoro-4-hydroxybenzoate (45 mg, 0.24 mmol) were mixed in 1 mL DCM. The mixture was cooled to 0° C. and DBAD (73 mg, 0.318 mmol) was added. The cooling bath was removed and the reaction was stirred for 3 hours. The polymer was removed by filtration and was washed thoroughly with acetone. The filtration was concentrated and purified by chromatography on silica eluting with 20% EtOAc/hexanes to give Example 1. LCMS calc: 421.40; obs: 422.02 (M+1); Human GPR119 EC$_{50}$: 28.74 nM.

Example 2

2,6-Difluoro-4-(2-{(1S,2R)-2-[1-(2,2,2-trifluoroethyl)piperidin-4-yl]cyclopropyl}ethoxy)benzoic acid

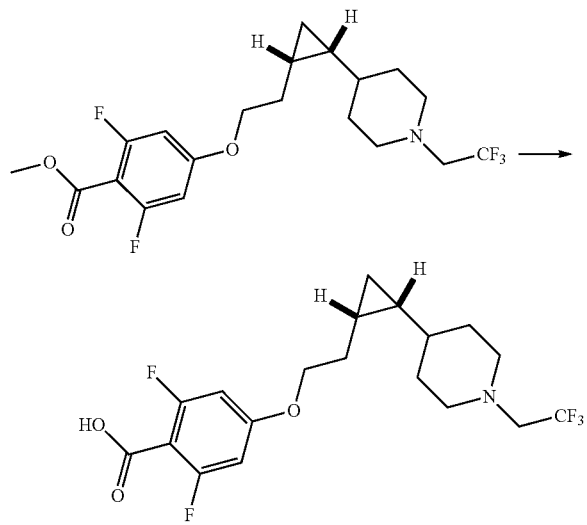

A solution of methyl 2,6-difluoro-4-(2-{(1S,2R)-2-[1-(2,2,2-trifluoroethyl)piperidin-4-yl]cyclopropyl}ethoxy)benzoate (16.0 mg, 0.038 mmol) in MeOH (0.75 mL) was treated with NaOH aqueous solution (0.076 mL, 5 M, 0.38 mmol). It was heated at 60° C. for 4 hours. The mixture was cooled to RT, acidified with 2N HCl, diluted with EtOAc, washed with water, brine, dried with sodium sulfate. The solvent was removed under reduced pressure to yield Example 2. LCMS calc: 407.37; obs: 408.01 (M+1).

Example 3

N-Cyclopropyl-2,6-difluoro-4-(2-{(1S,2R)-2-[1-(2,2,2-trifluoroethyl)piperidin-4-yl]cyclopropyl}ethoxy)benzamide

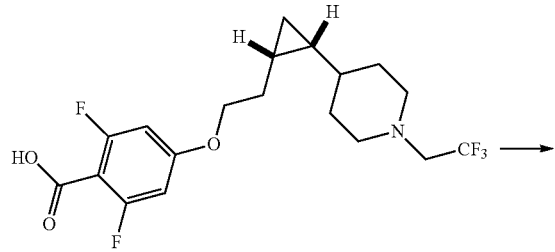

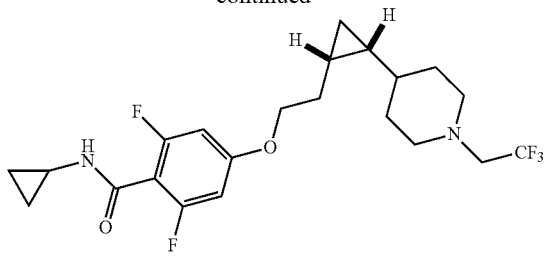

2,6-Difluoro-4-(2-{(1S,2R)-2-[1-(2,2,2-trifluoroethyl)piperidin-4-yl]cyclopropyl}ethoxy)benzoic acid (40 mg, 0.098 mmol) in 0.5 mL of DCM was stirred with EDC (37.6 mg, 0.196 mmol), HOBt (30 mg, 0.196 mmol) and DIPEA (64 mg, 0.49 mmol) at RT for 15 min. Cyclopropylamine (11.2 mg, 0.196 mmol) was added. The reaction mixture was stirred overnight. Solvent was removed under vacuum. The residue was purified by mass directed RPHPLC. The product fraction was basified with 2 M sodium bicarbonate aq. solution. The product was extracted with EtOAc. The organic layer was dried with sodium sulfate and concentrated to yield Example 3. LCMS calc: 446.45; obs: 447.01 (M+1); Human GPR119 EC$_{50}$: 5.28 nM.

$^1$H NMR (CDCl$_3$, 500 MHz) 6.48 (d, 2H), 6.09 (br, 1H), 4.5 (m, 2H), 2.95-3.03 (m, 4H), 2.34 (m, 2H), 2.12 (m, 1H), 1.75 (m, 3H), 1.5-1.62 (m, 3H), 0.92 (m, 3H), 0.81 (m, 1H), 0.6-0.7 (m, 4H), −0.85 (m, 1H)

Example 4

4-[(1R,2S)-2-{2-[4-(Methylsulfonyl)phenoxy]ethyl}cyclopropyl]-1-(2,2,2-trifluoroethyl)piperidine

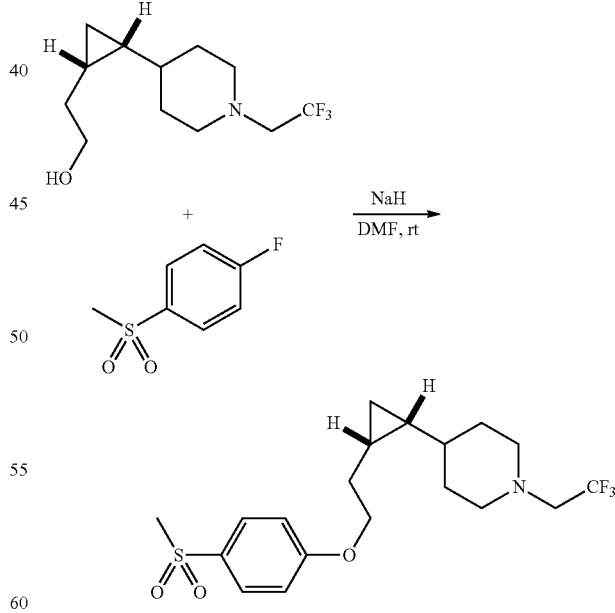

To a solution of 2-((1S,2R)-2-[1-(2,2,2-trifluoroethyl)piperidin-4-yl]cyclopropyl)ethanol (30 mg, 0.119 mmol) in DMF (1 mL) was added NaH (60%, 7.2 mg, 0.179 mmol) at RT. The mixture was stirred for 15 min. 1-fluoro-4-(methylsulfonyl)benzene (20.8 mg, 0.119 mmol) was added to the reaction mixture. It was heated at 50° C. for 3 hours. The reaction was quenched with water, extracted with EtOAc. The organic layer was dried by sodium sulfate and concentrated. The residue was purified by Mass directed RPHPLC. The product fraction was basified with 1 M sodium bicarbonate aq. solution, extracted with EtOAc. Solvent was removed under vacuum to yield the Example 4. LCMS calc: 405.47; obs: 406.04 (M+1); Human GPR119 $EC_{50}$: 175.6 nM. $^1$H NMR ($CDCl_3$, 500 MHz) 7.90 (d, 2H), 7.02 (d, 2H), 4.15 (m, 2H), 3.05 (s, 3H), 2.97 (m, 4), 2.34 (m, 2H), 2.18 (m, 1H), 1.78 (m, 2H), 1.45-1.58 (m, 3H), 0.96 (m, 1H), 0.82 (m, 1H), 0.65 (m, 2H), −0.88 (m, 1H)

Using a similar procedure for the preparation of Examples 1-4 the following compounds were prepared.

| Example | Structure | Observed Mass (M + H) | Human GPR119 $EC_{50}$ (nM) |
|---|---|---|---|
| 5 | 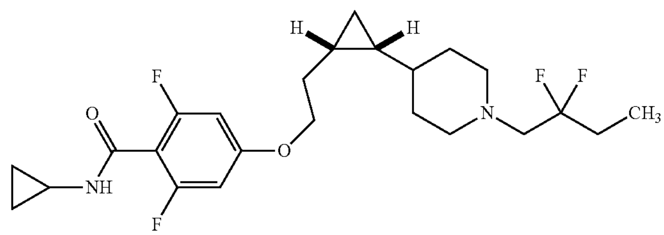 [SMILES: CCC(F)(F)CN1CCC([C@H]2C[C@H]2CCOc2cc(F)c(C(=O)NC3CC3)c(F)c2)CC1] | 457.13 | 0.43 |
| 6 | 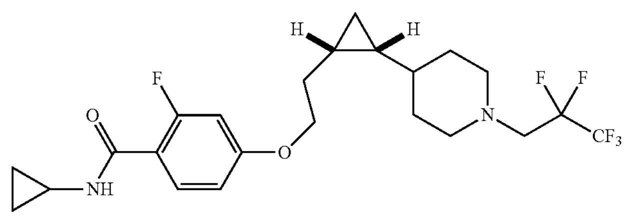 [SMILES: O=C(NC1CC1)c1ccc(OCC[C@@H]2C[C@@H]2C2CCN(CC(F)(F)C(F)(F)F)CC2)cc1F] | 479.05 | 0.52 |
| 7 | 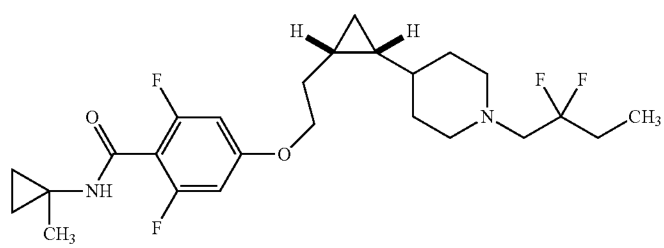 [SMILES: CCC(F)(F)CN1CCC([C@H]2C[C@H]2CCOc2cc(F)c(C(=O)NC3(C)CC3)c(F)c2)CC1] | 471.15 | 1.20 |
| 8 | 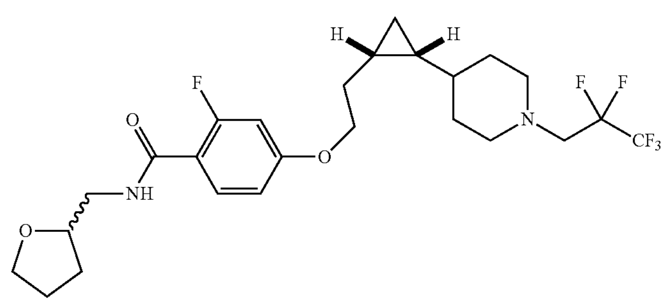 [SMILES: O=C(NCC1CCCO1)c1ccc(OCC[C@@H]2C[C@@H]2C2CCN(CC(F)(F)C(F)(F)F)CC2)cc1F] | — | 1.60 |
| 9 | 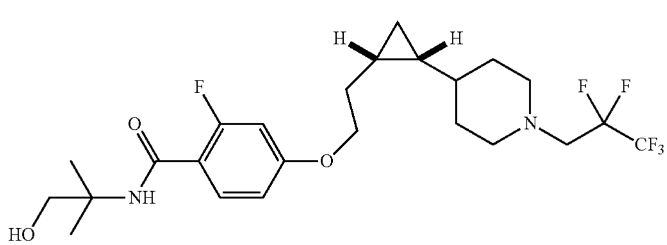 [SMILES: CC(C)(CO)NC(=O)c1ccc(OCC[C@@H]2C[C@@H]2C2CCN(CC(F)(F)C(F)(F)F)CC2)cc1F] | 511.12 | 2.34 |

-continued

| Example | Structure | Observed Mass (M + H) | Human GPR119 EC$_{50}$ (nM) |
|---------|-----------|------------------------|------------------------------|
| 10 | 2-fluoro-N-((1-hydroxycyclopropyl)methyl)-4-(2-((1R,2S)-2-(1-(2,2,2-trifluoroethyl)piperidin-4-yl)cyclopropyl)ethoxy)benzamide | 509.05 | 3.021 |
| 11 | N-cyclopropyl-2-fluoro-4-(2-((1R,2S)-2-(1-(2,2-difluoroethyl)piperidin-4-yl)cyclopropyl)ethoxy)benzamide | 461.11 | 3.16 |
| 12 | 2-fluoro-N-(isoxazol-4-ylmethyl)-4-(2-((1R,2S)-2-(1-(2,2,2-trifluoroethyl)piperidin-4-yl)cyclopropyl)ethoxy)benzamide | 520.07 | 3.69 |
| 13 | N-tert-butyl-2-fluoro-4-(2-((1R,2S)-2-(1-(2,2,2-trifluoroethyl)piperidin-4-yl)cyclopropyl)ethoxy)benzamide | — | 3.83 |
| 14 | 2-fluoro-1-(methylsulfonyl)-4-(2-((1R,2S)-2-(1-(2,2,2-trifluoroethyl)piperidin-4-yl)cyclopropyl)ethoxy)benzene | 474.18 | 4.35 |
| 15 | N-cyclopropyl-2,6-difluoro-4-(2-((1R,2S)-2-(1-(2,2,2-trifluoroethyl)piperidin-4-yl)cyclopropyl)ethoxy)benzamide | 447.01 | 5.28 |

-continued

| Example | Structure | Observed Mass (M + H) | Human GPR119 EC$_{50}$ (nM) |
| --- | --- | --- | --- |
| 16 | 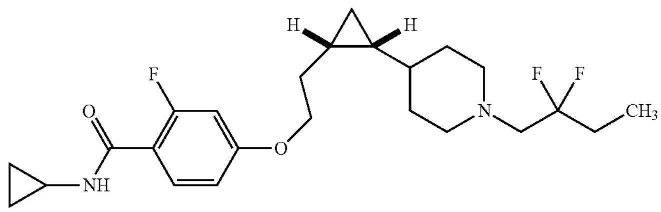 [SMILES: CCC(F)(F)CN1CCC([C@H]2C[C@H]2CCOc2ccc(C(=O)NC3CC3)c(F)c2)CC1] | 439.14 | 5.34 |
| 17 | 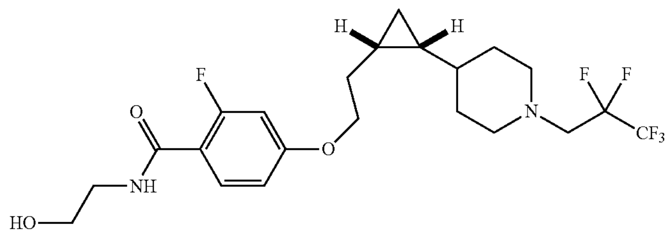 [SMILES: O=C(NCCO)c1ccc(OCC[C@@H]2C[C@@H]2C2CCN(CC(F)(F)C(F)(F)F)CC2)cc1F] | 483.04 | 5.38 |
| 18 | 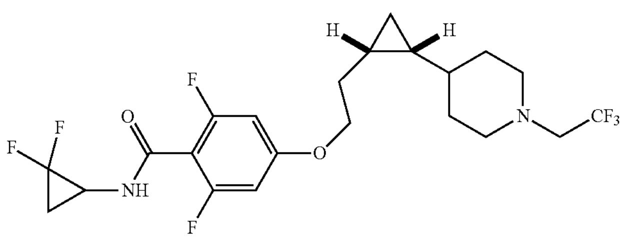 [SMILES: O=C(NC1CC1(F)F)c1c(F)cc(OCC[C@@H]2C[C@@H]2C2CCN(CC(F)(F)F)CC2)cc1F] | 483.26 | 5.87 |
| 19 | 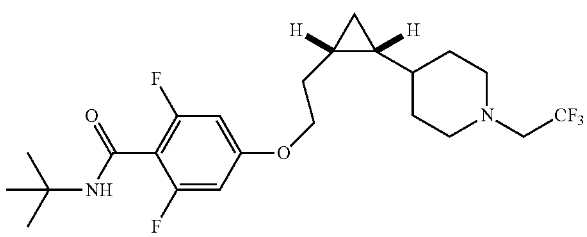 [SMILES: CC(C)(C)NC(=O)c1c(F)cc(OCC[C@@H]2C[C@@H]2C2CCN(CC(F)(F)F)CC2)cc1F] | 463.06 | 12.16 |
| 20 | 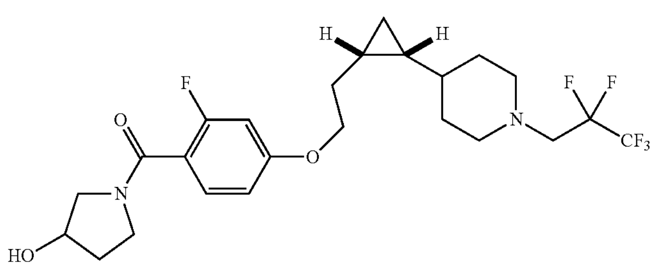 [SMILES: O=C(c1ccc(OCC[C@@H]2C[C@@H]2C2CCN(CC(F)(F)C(F)(F)F)CC2)cc1F)N1CCC(O)C1] | 509.03 | 13.36 |
| 21 | 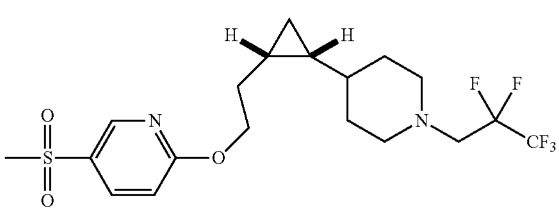 [SMILES: CS(=O)(=O)c1ccc(OCC[C@@H]2C[C@@H]2C2CCN(CC(F)(F)C(F)(F)F)CC2)nc1] | 457.03 | 14.0 |

-continued

| Example | Structure | Observed Mass (M + H) | Human GPR119 EC$_{50}$ (nM) |
|---|---|---|---|
| 22 | 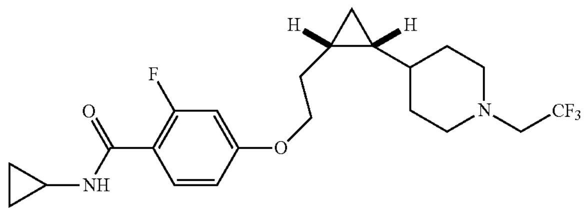 [SMILES: O=C(NC1CC1)c1ccc(OCC[C@@H]2C[C@@H]2C2CCN(CC(F)(F)F)CC2)cc1F] | 429.06 | 16.65 |
| 23 | 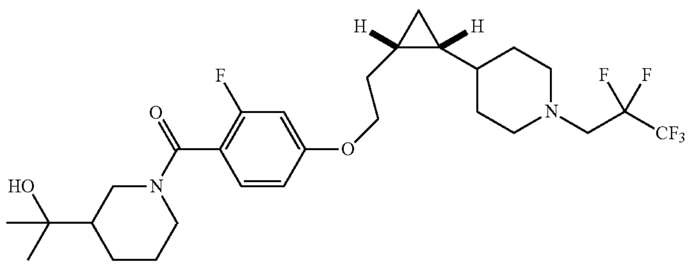 [SMILES: CC(C)(O)C1CCCN(C(=O)c2ccc(OCC[C@@H]3C[C@@H]3C3CCN(CC(F)(F)C(F)(F)F)CC3)cc2F)C1] | 565.19 | 18.42 |
| 24 | 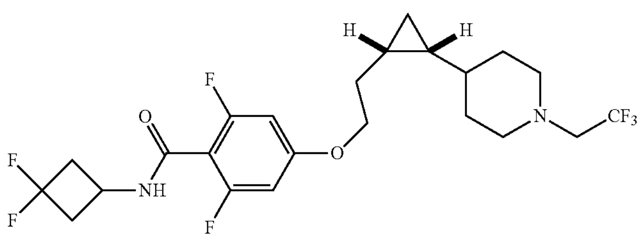 [SMILES: O=C(NC1CC(F)(F)C1)c1c(F)cc(OCC[C@@H]2C[C@@H]2C2CCN(CC(F)(F)F)CC2)cc1F] | 497.20 | 20.25 |
| 25 | 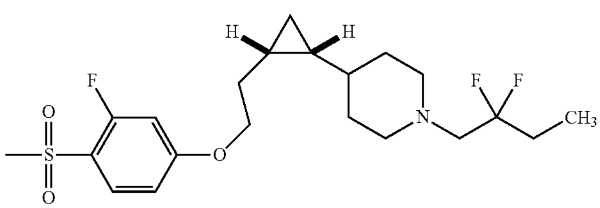 [SMILES: CCC(F)(F)CN1CCC([C@H]2C[C@H]2CCOc2ccc(S(C)(=O)=O)c(F)c2)CC1] | 434.11 | 22.46 |
| 26 | 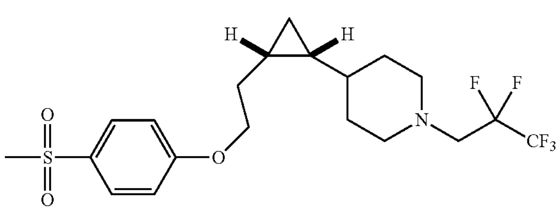 | 455.97 | 23.64 |
| 27 | 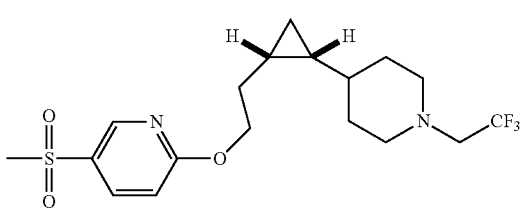 | 407 | 27.76 |

| Example | Structure | Observed Mass (M + H) | Human GPR119 EC$_{50}$ (nM) |
|---|---|---|---|
| 28 | 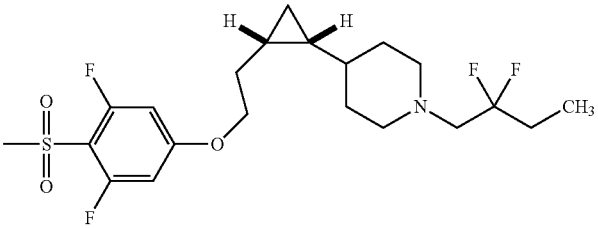 [SMILES: CCC(F)(F)CN1CCC([C@H]2C[C@H]2CCOc2cc(F)c(S(C)(=O)=O)c(F)c2)CC1] | 452.1 | 35.26 |
| 29 | 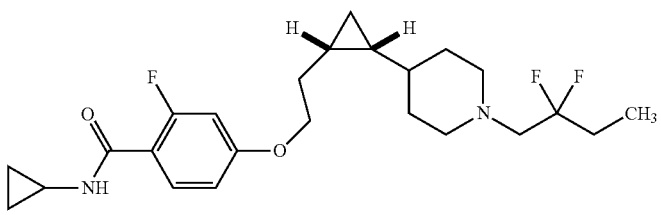 [SMILES: CCC(F)(F)CN1CCC([C@H]2C[C@H]2CCOc2ccc(C(=O)NC3CC3)c(F)c2)CC1] | 425.07 | 45.09 |
| 30 | 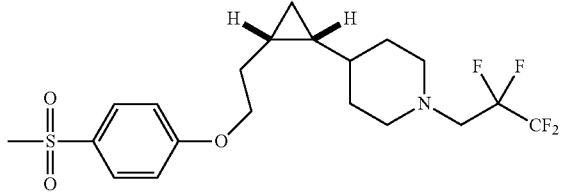 | — | 45.35 |
| 31 | 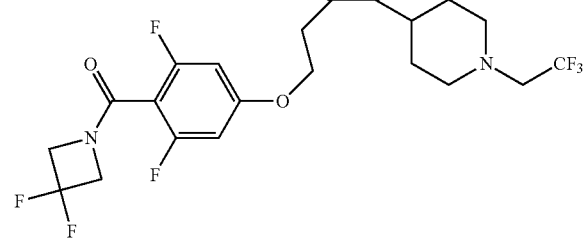 | 483.16 | 45.81 |
| 32 | 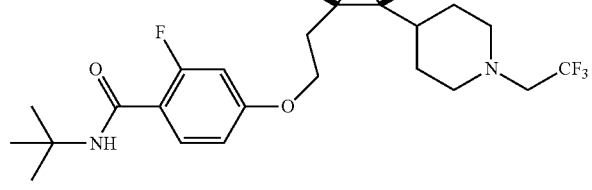 | 445.07 | 57.89 |
| 33 | 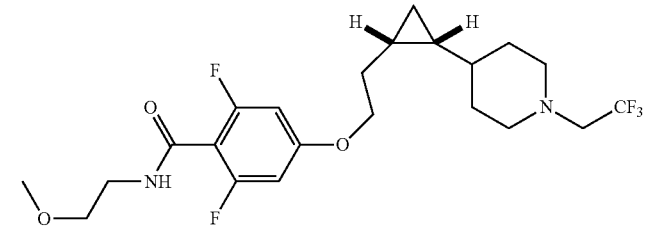 [SMILES: COCCNC(=O)c1c(F)cc(OCC[C@@H]2C[C@@H]2C2CCN(CC(F)(F)F)CC2)cc1F] | 465.03 | 68.02 |

-continued

| Example | Structure | Observed Mass (M + H) | Human GPR119 EC$_{50}$ (nM) |
|---|---|---|---|
| 34 | 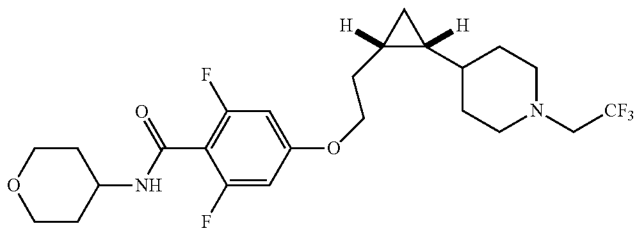 [SMILES: O=C(NC1CCOCC1)c1c(F)cc(OCC[C@@H]2C[C@@H]2C2CCN(CC(F)(F)F)CC2)cc1F] | 491.11 | 77.28 |
| 35 | 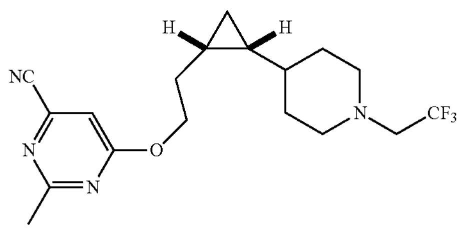 [SMILES: Cc1nc(C#N)cc(OCC[C@@H]2C[C@@H]2C2CCN(CC(F)(F)F)CC2)n1] | 369.11 | 125.70 |
| 36 | 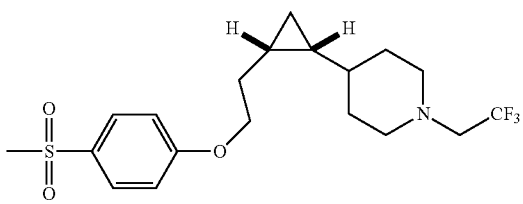 [SMILES: CS(=O)(=O)c1ccc(OCC[C@@H]2C[C@@H]2C2CCN(CC(F)(F)F)CC2)cc1] | 406.04 | 175.60 |
| 37 | 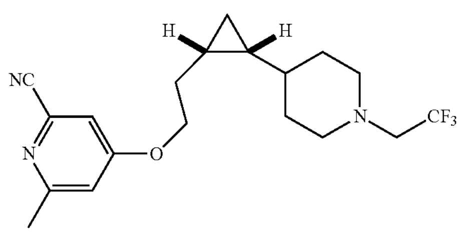 [SMILES: Cc1cc(OCC[C@@H]2C[C@@H]2C2CCN(CC(F)(F)F)CC2)cc(C#N)n1] | 368.09 | 198.90 |
| 38 | 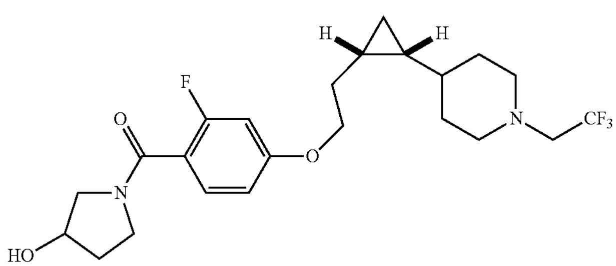 [SMILES: O=C(c1ccc(OCC[C@@H]2C[C@@H]2C2CCN(CC(F)(F)F)CC2)cc1F)N1CCC(O)C1] | 459.05 | 257.40 |
| 39 | 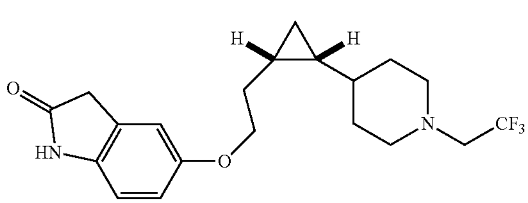 [SMILES: O=C1Cc2cc(OCC[C@@H]3C[C@@H]3C3CCN(CC(F)(F)F)CC3)ccc2N1] | 383.17 | 270.00 |

| Example | Structure | Observed Mass (M + H) | Human GPR119 EC$_{50}$ (nM) |
|---|---|---|---|
| 40 | 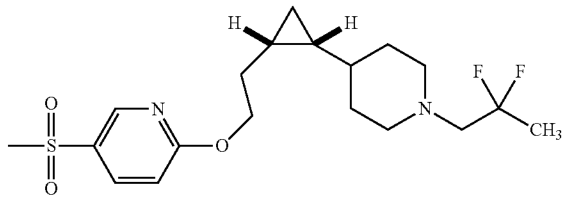 [SMILES: CC(F)(F)CN1CCC([C@H]2C[C@H]2CCOc2ccc(S(C)(=O)=O)cn2)CC1] | 403.04 | 775.50 |
| 41 | 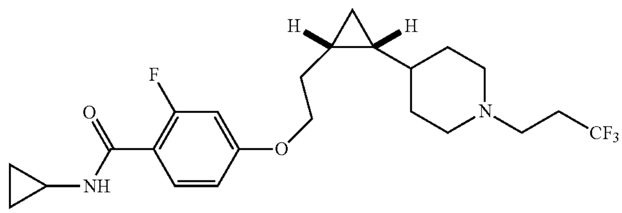 [SMILES: O=C(NC1CC1)c1ccc(OCC[C@@H]2C[C@@H]2C2CCN(CCC(F)(F)F)CC2)cc1F] | 443.03 | 59.32 |
| 42 | 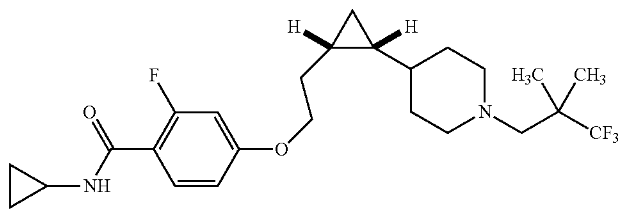 [SMILES: CC(C)(CN1CCC([C@H]2C[C@H]2CCOc2ccc(C(=O)NC3CC3)c(F)c2)CC1)C(F)(F)F] | 471.12 | 2.34 |
| 43 | 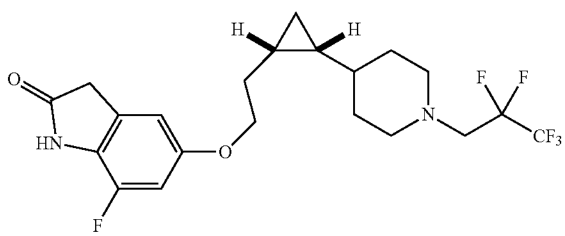 [SMILES: O=C1Cc2cc(OCC[C@@H]3C[C@@H]3C3CCN(CC(F)(F)C(F)(F)F)CC3)cc(F)c2N1] | 451.25 | 7.13 |
| 44 | 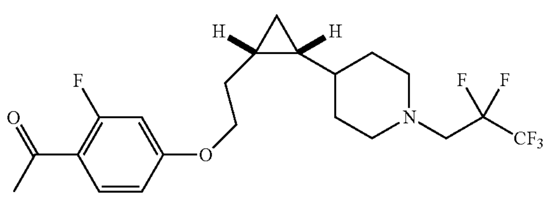 [SMILES: CC(=O)c1ccc(OCC[C@@H]2C[C@@H]2C2CCN(CC(F)(F)C(F)(F)F)CC2)cc1F] | 438 | 51.56 |
| 45 | 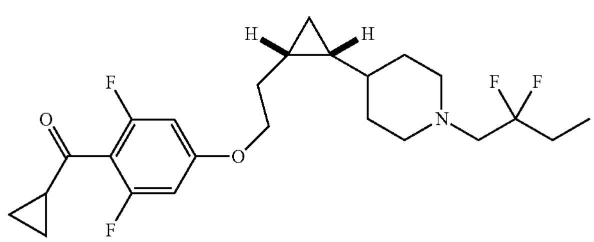 [SMILES: CCC(F)(F)CN1CCC([C@H]2C[C@H]2CCOc2cc(F)c(C(=O)C3CC3)c(F)c2)CC1] | 442.25 | 1.65 |
| 46 | 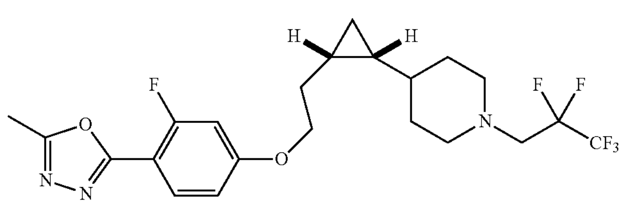 [SMILES: Cc1nnc(-c2ccc(OCC[C@@H]3C[C@@H]3C3CCN(CC(F)(F)C(F)(F)F)CC3)cc2F)o1] | — | 7.31 |

-continued

| Example | Structure | Observed Mass (M + H) | Human GPR119 EC$_{50}$ (nM) |
|---|---|---|---|
| 47 | 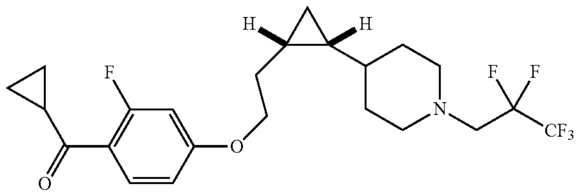 [SMILES: O=C(c1ccc(OCC[C@@H]2C[C@@H]2C2CCN(CC(F)(F)C(F)(F)F)CC2)cc1F)C1CC1] | 425.28 | 10.17 |
| 48 | 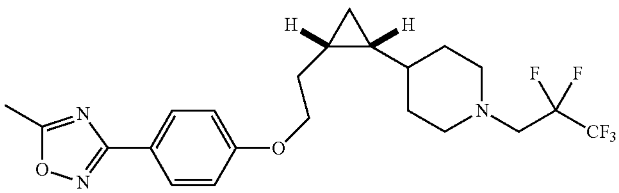 [SMILES: Cc1nc(-c2ccc(OCC[C@@H]3C[C@@H]3C3CCN(CC(F)(F)C(F)(F)F)CC3)cc2)no1] | 433.97 | 17.46 |
| 49 | 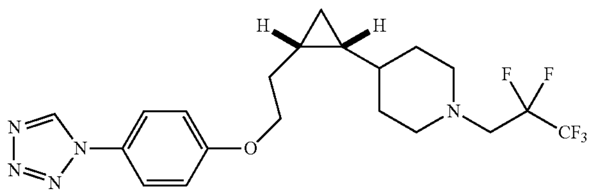 [SMILES: FC(F)(F)C(F)(F)CN1CCC([C@H]2C[C@H]2CCOc2ccc(-n3cncn3)cc2)CC1] | 446.06 | 24.22 |
| 50 | 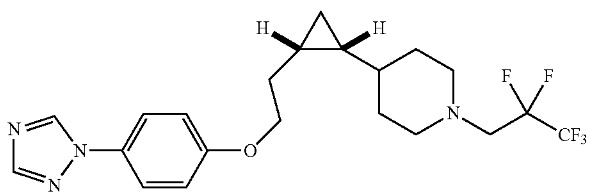 | 445.07 | 26.85 |
| 51 | 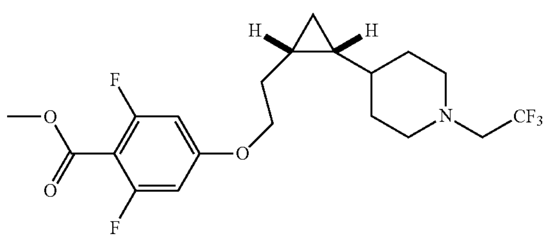 [SMILES: COC(=O)c1c(F)cc(OCC[C@@H]2C[C@@H]2C2CCN(CC(F)(F)F)CC2)cc1F] | 422.02 | 28.74 |
| 52 | 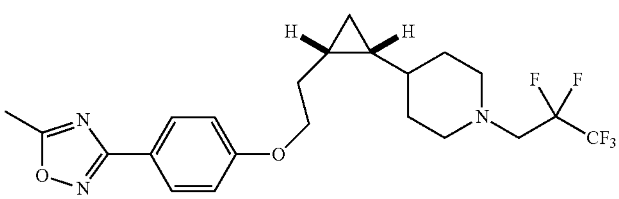 [SMILES: Cc1nc(-c2ccc(OCC[C@@H]3C[C@@H]3C3CCN(CC(F)(F)C(F)(F)F)CC3)cc2)no1] | 460.08 | 40.79 |
| 53 | 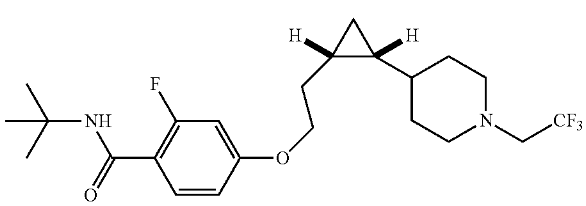 [SMILES: CC(C)(C)NC(=O)c1ccc(OCC[C@@H]2C[C@@H]2C2CCN(CC(F)(F)F)CC2)cc1F] | 445.07 | 57.89 |

| Example | Structure | Observed Mass (M + H) | Human GPR119 EC$_{50}$ (nM) |
|---|---|---|---|
| 54 | 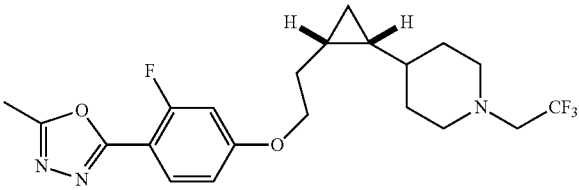 [SMILES: Cc1nnc(-c2ccc(OCC[C@@H]3C[C@@H]3C3CCN(CC(F)(F)F)CC3)cc2F)o1] | 428.04 | 59.48 |
| 55 | 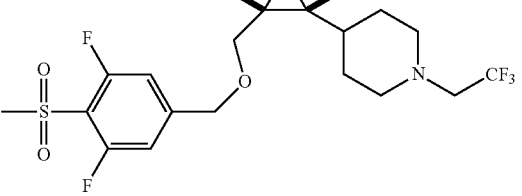 | 441.83 | 567.9 |
| 56 | 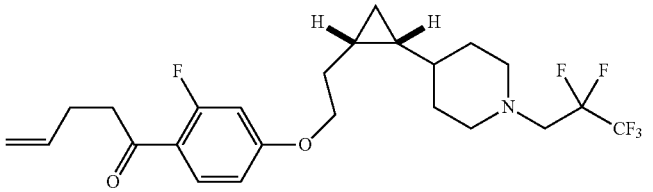 [SMILES: C=CCCC(=O)c1ccc(OCC[C@@H]2C[C@@H]2C2CCN(CC(F)(F)C(F)(F)F)CC2)cc1F] | 478.22 | 13.36 |

Evaluation of Glucose Dependent Insulin Secretion (GDIS) in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, 1967 Diabetes 16-35-39). The islets were cultured overnight in RPMI 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 Na$^+$, 5.8 K$^+$, 2.5 Ca$^{2+}$, 1.2 Mg$^{2+}$, 124.1 Cl$^-$, 1.2 PO$_4^{3-}$, 1.2 SO$_4^{2+}$, 25CO$_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 μl KRB medium). The compounds were added to KRB medium just before the initiation of the 60-min incubation. Insulin concentration in aliquots of the incubation buffer was measured by the ultra-sensitive rat insulin EIA kit from ALPCO Diagnostics (Windham, N.H.).

Compounds of the present invention were shown to be biologically active in one or more of the following assays:
Measurement of GPR119 Signaling (Cyclic AMP (cAMP) Assay)

Human embryonic kidney (HEK) 293 cell lines stably transfected with human GPR119 were maintained in Dulbecco's Modified Eagle Medium (DMEM) containing fetal bovine serum (FBS), penicillin-streptomycin, HEPES buffer (4-(2-hydroxyethyl)-1-piperazineethane sulfonic acid), and hygromycin. For the cAMP assay, the transfected cells were harvested using a non-enzymatic cell dissociation solution (GIBCO 2672), pelleted and resuspended in stimulation buffer (DMEM, 25 mM HEPES, 0.1% bovine serum albumin (BSA), pH 7.4 in the presence of 100 μM phosphodiesterase inhibitors). The adenylate cyclase assay was constructed following the LANCE™ cAMP Kit (Perkin Elmer, AD0264) instructions.

Briefly, cells with Alexa Fluor® 647-anti cAMP antibody were incubated with 10 point series diluted test article in stimulation buffer with a final concentration of 2.5% DMSO for 45 minutes. The reaction was stopped by incubating with the supplied detection buffer containing the europium chelate of the Eu-SA/Biotin-cAMP tracer for 3 hours. The assay was performed in duplicate in a 384 well plate for duplicate plates and fluorescence was measured at 665 nm. Basal activity was determined using a DMSO control and maximum response was defined as cAMP stimulation produced by an internal agonist control. Standard cAMP concentrations were assayed concurrently for conversion of fluorescence signal to cAMP level. The data was analyzed using 4-parameter curve fit in Microsoft Excel.

Measurement of GPR119 Signaling (cAMP Homogenous Time Resolved Fluorescence (HTRF) Assay)

Chinese hamster ovary (CHO) cell lines stably transfected with the permissive guanine nucleotide binding protein alpha 15 (Gα15) and murine GPR119 were maintained in DMEM media containing FBS, penicillin-streptomycin, puromycin, and G418 (geneticin). Alternatively, human embryonic kidney (HEK) 293 Flp-In cells (Invitrogen, Carlsbad, Calif.) were stably transfected with a human SNP variant (S309L) of GPR119 and maintained in DMEM media containing FBS, penicillin-streptomycin, and hygromycin. Agonist activation of the GPR119 receptor was measured in receptor transfected cells described above, treated with compounds of this invention, using a commercial homogenous time resolved fluorescence (HTRF) kit for measurement of cAMP (CisBio, Bedford, Mass.). The assay was performed in 96-well half-volume plates (murine) or 384-well plates (human) following the manufacturers instructions. Briefly, suspended cells were incubated with a dose titration of test compound at RT for 60 min, lysed, and incubated with HTRF reagents for an additional 60 min. The plate was read using an Envision multilabel reader (Perkin Elmer) adjusted to read time resolved fluorescence and the cAMP concentrations were extrapolated from a cAMP calibration curve. GPR119 agonists exhibit a concentration-dependent increase in intracellular cAMP. The concentration of test compound required to stimulate a half-maximal response (EC50), and efficacy as compared to an internal agonist control, was determined from a sigmoidal 4-parameter curve fit of the resulting plot of normalized activity versus compound concentration.

Evaluation of GDIS in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, Diabetes (16) 35-39 (1967)). The islets were cultured overnight in RPMI 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 $Na^+$, 5.8 $K^+$, 2.5 $Ca^{2+}$, 1.2 $Mg^{2+}$, 124.1 Cr, 1.2 $PO_4^{3-}$, 1.2 $SO_4^{2+}$, 25 $CO_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 µl KRB medium). The compounds were added to KRB medium just before the initiation of the 60-min incubation. Insulin concentration in aliquots of the incubation buffer was measured by the ultrasensitive rat insulin EIA kit from ALPCO Diagnostics (Windham, N.H.).

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size 0 hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound represented by the formula:

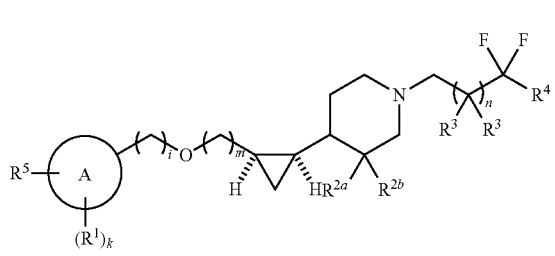

or a pharmaceutically acceptable salt thereof, wherein:
ring A is
(1) aryl,
(2) 9 or 10-membered fused aryl, wherein aryl is fused with a heteroaryl or heterocyclyl group,
(3) 6-membered heteroaryl, or
(4) 9 or 10-membered fused heteroaryl,
wherein the heteroaryl or heterocyclyl groups contain 1-2 N atoms;
i or n are independently 0 or 1;
m is 1 or 2;
k is 0, 1, 2, or 3;
each $R^1$ is selected from the group consisting of
(1) halo,
(2) $C_{1-6}$ alkyl,
(3) halo$C_{1-6}$ alkyl
(4) hydroxyl,
(5) $C_{1-6}$ alkoxyl, and
(6) amino,
wherein the alkyl group is unsubstituted or substituted by hydroxy, $C_{1-3}$alkoxy, or halo;
$R^{2a}$ and $R^{2b}$ are independently hydrogen or halo;
each $R^3$ is independently hydrogen, halo, $C_{1-6}$alkyl, or halo$C_{1-6}$alkyl;
$R^4$ is hydrogen, halo, $C_{1-6}$alkyl, or halo$C_{1-6}$alkyl; and
$R^5$ is selected from the group consisting of
(1) oxo,
(2) —COOH,
(3) —NH—C(O)$C_{1-6}$alkyl,
(4) —C(O)$C_{1-6}$alkyl,
(5) —C(O)$_2C_{1-6}$alkyl,
(6) —C(O)$C_{1-3}$alkyl-heteroaryl,
(7) —C(O)$C_{1-3}$alkyl-heterocyclyl,
(8) —C(O)heterocyclyl,
(9) —C(O)$C_{3-6}$cycloalkyl,
(10) —C(O)NH—$C_{1-6}$alkyl,
(11) —C(O)NH—$C_{2-6}$alkenyl,
(12) —C(O)NH—$C_{3-6}$cycloalkyl,
(13) —C(O)NH-heterocyclyl,
(14) —C(O)NH—$C_{1-3}$alkyl-$C_{3-6}$cycloalkyl,
(15) —C(O)NH$C_{1-3}$alkyl-heterocyclyl,
(16) —C(O)NH$C_{1-3}$alkyl-heteroaryl,
(17) —SO$_2C_{1-6}$alkyl,
(18) heteroaryl, and
(19) CN;
wherein the heteroaryl group is a 5- or 6-membered ring, containing 1-4 N, O, or S atoms;
wherein the heterocyclyl group is a 3- to 6-membered ring, containing 1-2 N or O atoms; wherein the alkyl group is unsubstituted or substituted by hydroxy, $C_{1-3}$alkoxy, or halo; and wherein the cycloalkyl, heterocyclyl, or heteroaryl groups are unsubstituted or substituted with 1-3 $C_{1-6}$alkyl, halo, hydroxy, hydroxy$C_{1-6}$alkyl, or $C_{1-6}$alkoxyl groups.

2. The compound of claim 1, or a pharmaceutically acceptable salt thereof, wherein ring A is aryl, 9 or 10-membered fused aryl, wherein aryl is fused with a heterocyclyl group, or 6-membered heteroaryl, wherein the heteroaryl or heterocyclyl groups contain 1-2 N atoms.

3. The compound of claim 2, or a pharmaceutically acceptable salt thereof, wherein ring A is phenyl, 2,3-dihydro-indolyl, pyridinyl, or pyrimidinyl.

4. The compound of claim 3, or a pharmaceutically acceptable salt thereof, wherein ring A is phenyl.

5. The compound of claim 1, or a pharmaceutically acceptable salt thereof, wherein $R^5$ is selected from the group consisting of
(1) oxo,
(2) —COOH,
(3) —C(O)$C_{1-6}$alkyl,
(4) —C(O)$_2C_{1-6}$alkyl,
(5) —C(O)$C_{1-3}$alkyl-heteroaryl,
(6) —C(O)$C_{1-3}$alkyl-heterocyclyl,
(7) —C(O)-heterocyclyl,
(8) —C(O)$C_{3-6}$cycloalkyl,
(9) —C(O)NH$C_{1-6}$alkyl,
(10) —C(O)NH$C_{2-6}$alkenyl,
(11) —C(O)NH$C_{3-6}$cycloalkyl,
(12) —C(O)NH-heterocyclyl,
(13) —C(O)NH$C_{1-3}$alkyl-heterocyclyl,
(14) —C(O)NH$C_{1-3}$alkyl-heteroaryl,
(15) —C(O)NH$C_{1-3}$alkyl-$C_{3-6}$cyclo alkyl,
(16) —SO$_2C_{1-4}$alkyl,
(17) heteroaryl, and
(18) CN;
wherein the heteroaryl group is a 5- or 6-membered ring, containing 1-4 N, O, or S atoms;
wherein the heterocyclyl group is a 3- to 6-membered ring, containing 1-2 N or O atoms; wherein the alkyl group is unsubstituted or substituted by hydroxy, $C_{1-3}$alkoxy, or halo; and wherein the cycloalkyl, heterocyclyl, or heteroaryl groups are unsubstituted or substituted with 1-3 $C_{1-6}$alkyl, halo, hydroxy, hydroxy$C_{1-6}$alkyl, or $C_{1-6}$alkoxyl groups.

6. The compound of claim 5, or a pharmaceutically acceptable salt thereof, wherein $R^5$ is selected from the group consisting of oxo, cyano 7. The compound of claim 1, or a pharmaceutically acceptable salt thereof, wherein $R^{2a}$ and $R^{2b}$ are independently hydrogen or fluoro.

8. The compound of claim 1, or a pharmaceutically acceptable salt thereof, wherein $R^4$ is fluoro, methyl, ethyl, difluoromethyl, or trifluoromethyl.

9. The compound of claim 1, or a pharmaceutically acceptable salt thereof, wherein each $R^3$ is independently hydrogen, fluoro or methyl.

10. The compound of claim 1, or a pharmaceutically acceptable salt thereof, wherein $R^1$ is fluoro or methyl.

11. The compound of claim 1, or a pharmaceutically acceptable salt thereof, wherein i is 0; and m is 1.

12. The compound of claim 1 represented by the formula:

I-A or a pharmaceutically acceptable salt thereof, wherein:
n is 0 or 1;
k is 0, 1, 2, or 3;
$R^1$ is selected from the group consisting of fluoro, and methyl;
$R^{2a}$ and $R^{2b}$ are independently hydrogen or halo;
each $R^3$ is independently hydrogen, fluoro or methyl;
$R^4$ is fluoro, methyl, ethyl, difluoromethyl, or trifluoromethyl; and
$R^5$ is selected from the group consisting of
(1) oxo,
(2) —COOH, (3) —C(O)C$_{1-6}$alkyl,
(4) —C(O)$_2$C$_{1-6}$alkyl,
(5) —C(O)C$_{1-3}$alkyl-heteroaryl,
(6) —C(O)C$_{1-3}$alkyl-heterocyclyl,
(7) —C(O)-heterocyclyl,
(8) —C(O)C$_{3-6}$cycloalkyl,
(9) —C(O)NHC$_{1-6}$alkyl,
(10) —C(O)NHC$_{2-6}$alkenyl,
(11) —C(O)NHC$_{3-6}$cycloalkyl,
(12) —C(O)NH-heterocyclyl,
(13) —C(O)NHC$_{1-3}$alkyl-heterocyclyl,
(14) —C(O)NHC$_{1-3}$alkyl-heteroaryl,
(15) —C(O)NHC$_{1-3}$alkyl-C$_{3-6}$cycloalkyl,
(16) —SO$_2$C$_{1-4}$alkyl,
(17) heteroaryl, and
(18) CN;
wherein the heteroaryl group is a 5- or 6-membered ring, containing 1-4 N, O, or S atoms; wherein the heterocyclyl group is a 3- to 6-membered ring, containing 1-2 N or O atoms; wherein the alkyl group is unsubstituted or substituted by hydroxy, C$_{1-3}$alkoxy, or halo; and wherein the cycloalkyl, heterocyclyl, or heteroaryl groups are unsubstituted or substituted with 1-3 C$_{1-6}$alkyl, halo, hydroxy, hydroxyC$_{1-6}$alkyl, or C$_{1-6}$alkoxyl groups.

13. The compound of claim 1 represented by the formula:

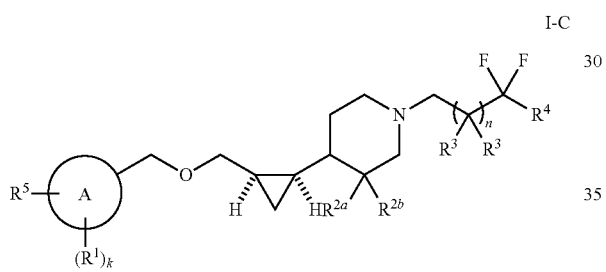

I-C or pharmaceutically acceptably salt thereof, wherein:
ring A is selected form the group consisting of pyridinyl or pyrimidinyl;
n is 0 or 1;
k is 0, 1, 2, or 3;
R$^1$ is selected from the group consisting of fluoro, and methyl;
R$^{2a}$ and R$^{2b}$ are independently hydrogen or halo;
each R$^3$ is independently hydrogen, fluoro or methyl;
R$^4$ is fluoro, methyl, ethyl, difluoromethyl, or trifluoromethyl; and
R$^5$ is selected from the group consisting of
(1) oxo,
(2) —COOH,
(3) —C(O)C$_{1-6}$alkyl,
(4) —C(O)$_2$C$_{1-6}$alkyl,
(5) —C(O)C$_{1-3}$alkyl-heteroaryl,
(6) —C(O)C$_{1-3}$alkyl-heterocyclyl,
(7) —C(O)heterocyclyl,
(8) —C(O)C$_{3-6}$cycloalkyl,
(9) —C(O)NHC$_{1-6}$alkyl,
(10) —C(O)NHC$_{2-6}$alkenyl,
(11) —C(O)NHC$_{3-6}$cycloalkyl,
(12) —C(O)NH-heterocyclyl,
(13) —C(O)NHC$_{1-3}$alkyl-heterocyclyl,
(14) —C(O)NHC$_{1-3}$alkyl-heteroaryl,
(15) —C(O)NHC$_{1-3}$alkyl-C$_{3-6}$cycloalkyl,
(16) —SO$_2$C$_{1-4}$alkyl,
(17) heteroaryl, and
(18) CN;
wherein the heteroaryl group is a 5- or 6-membered ring, containing 1-4 N, O, or S atoms; wherein the heterocyclyl group is a 3- to 6-membered ring, containing 1-2 N or O atoms;
wherein the alkyl group is unsubstituted or substituted by hydroxy, C$_{1-3}$alkoxy, or halo; and wherein the cycloalkyl, heterocyclyl, or heteroaryl groups are unsubstituted or substituted with 1-3 C$_{1-6}$alkyl, halo, hydroxy, hydroxyC$_{1-6}$alkyl, or C$_{1-6}$ alkoxyl groups.

14. The compound of claim 1 selected from the group consisting of:

1

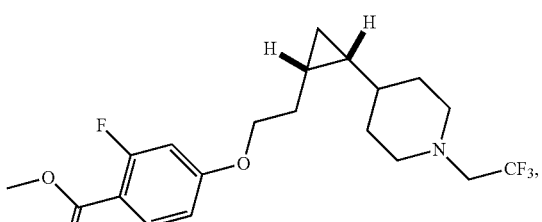

2

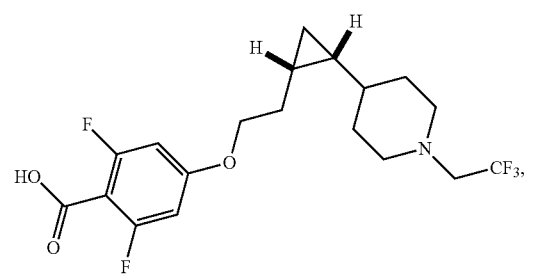

3

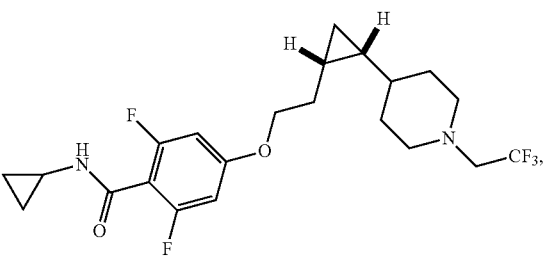

4

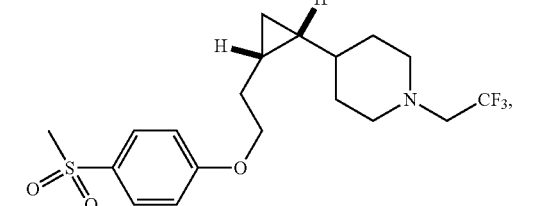

5

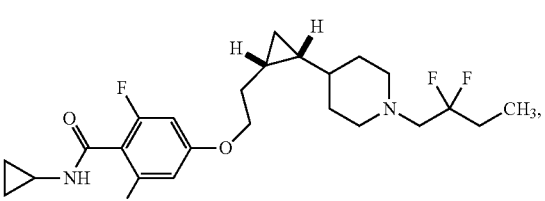

6
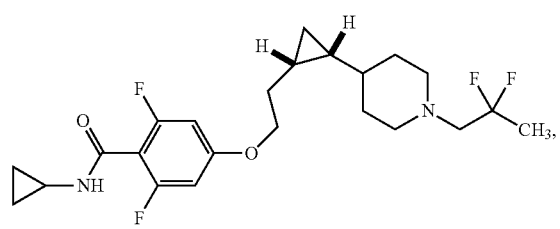
7
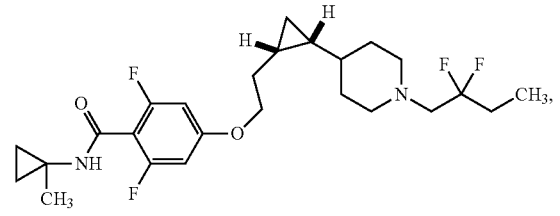
8
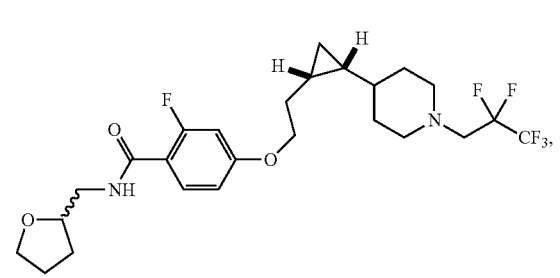
9
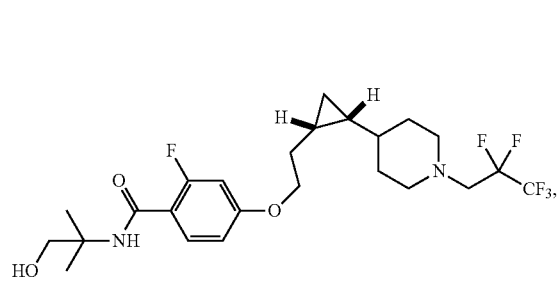
10
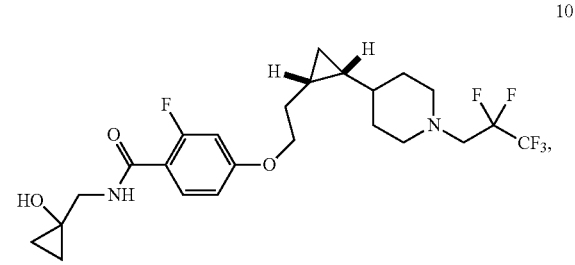
11
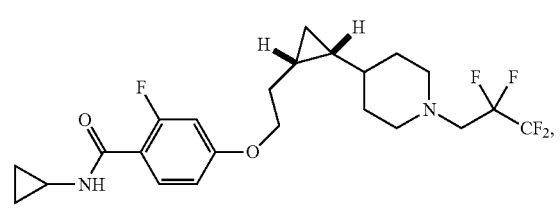
12
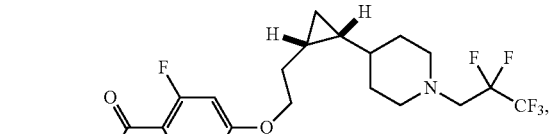
13
14
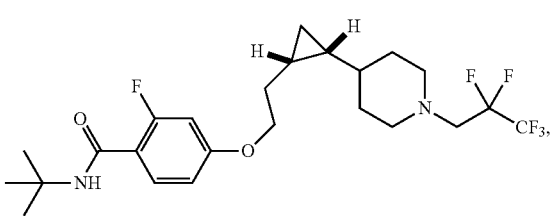
15
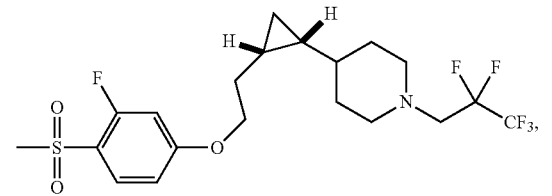
16
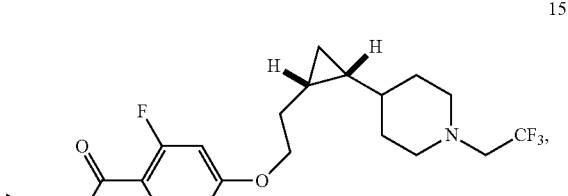
17
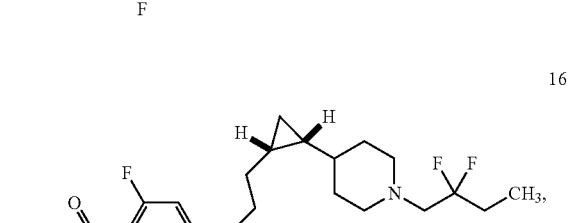

18
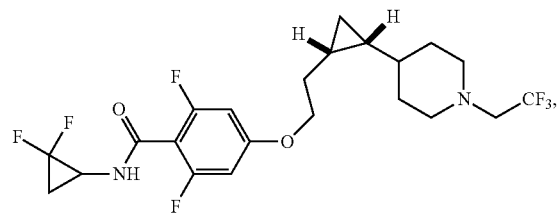
19
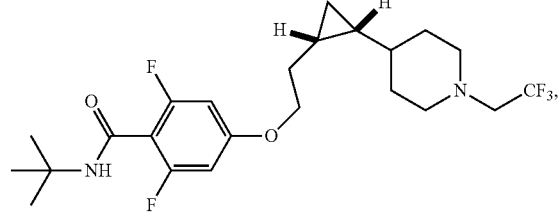
20
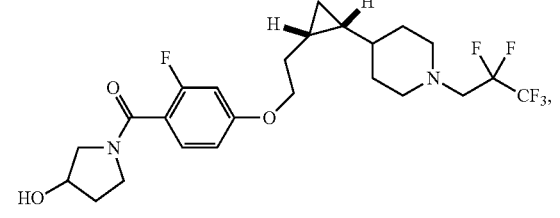
21
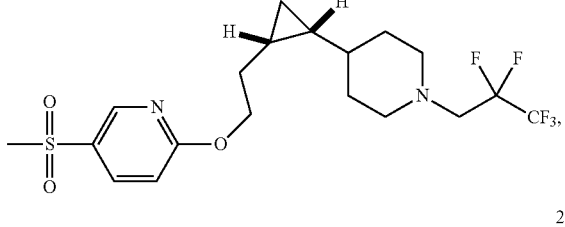
22
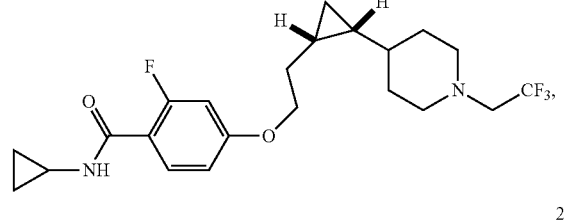
23
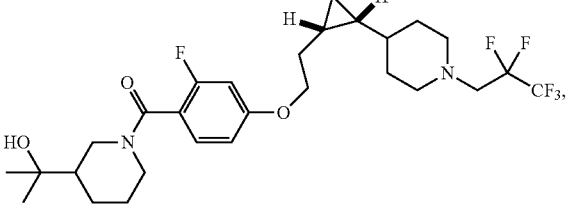
24
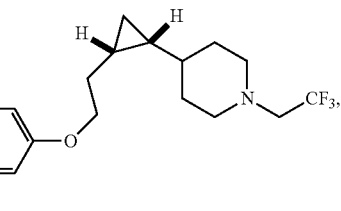
25
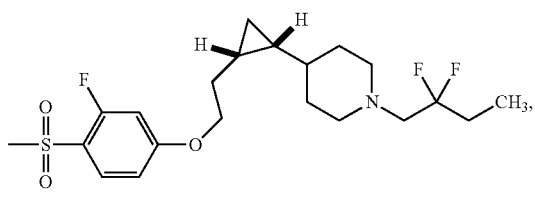
26
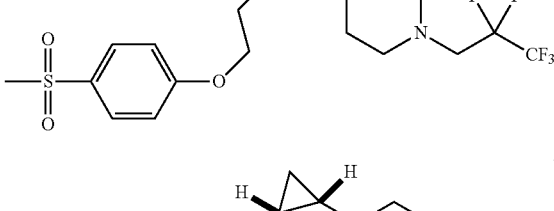
27
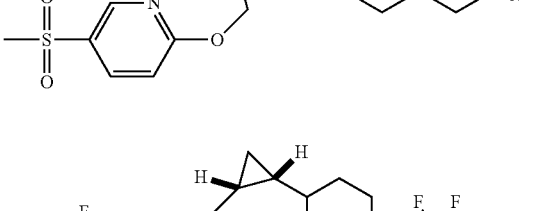
28
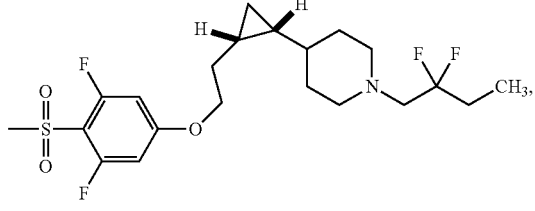
29
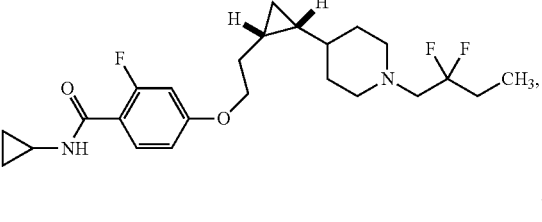
30
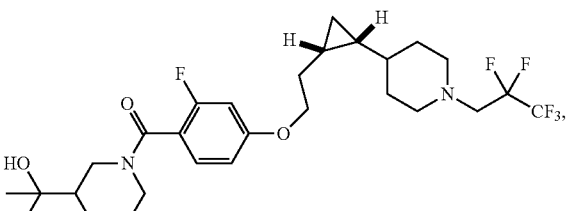

31
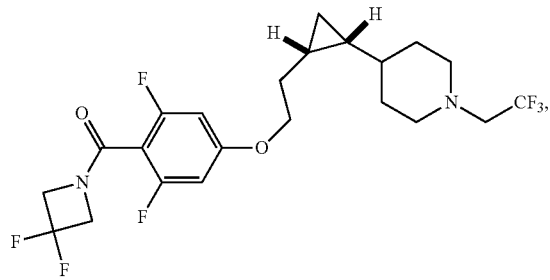
32
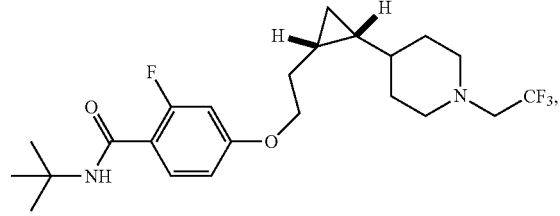
33
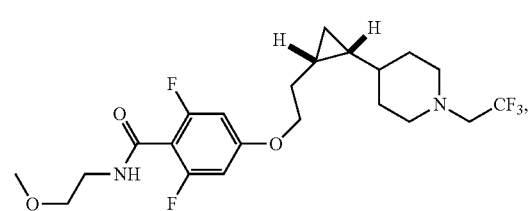
34
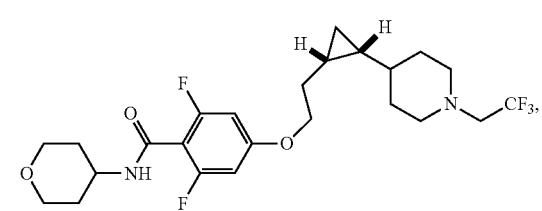
35
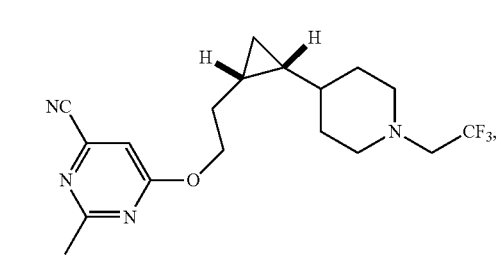
36
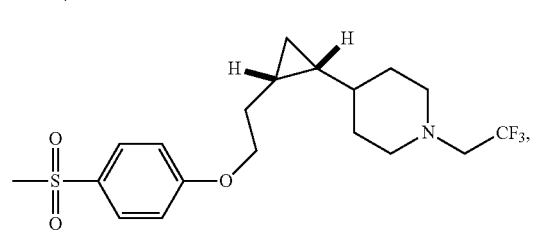
37
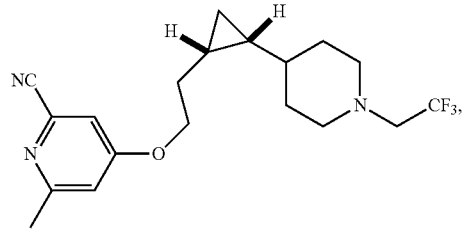
38
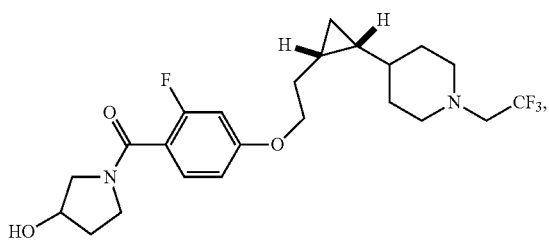
39
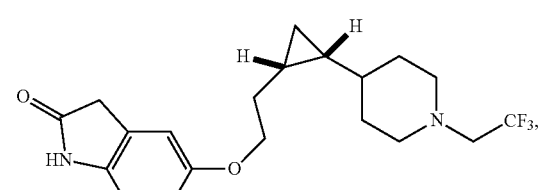
40
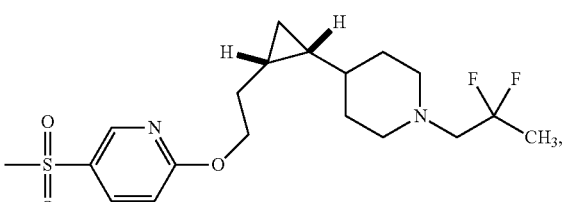
41
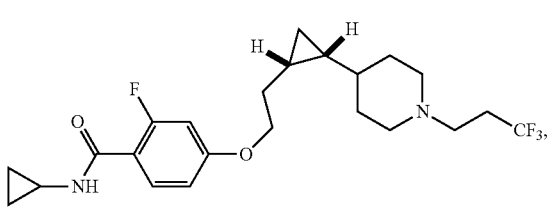
42
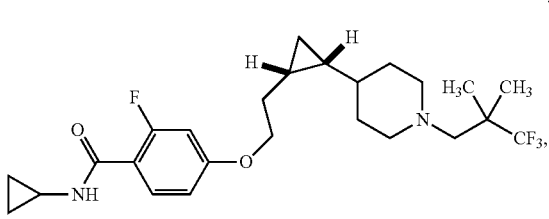

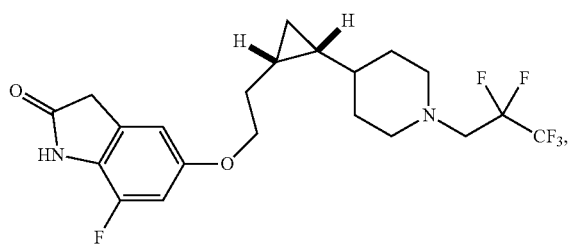
43
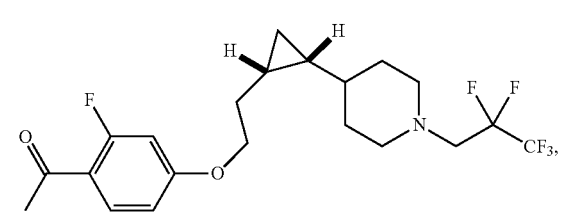
44
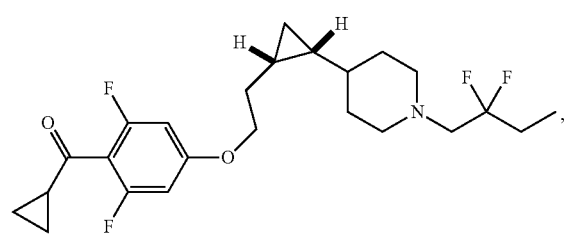
45
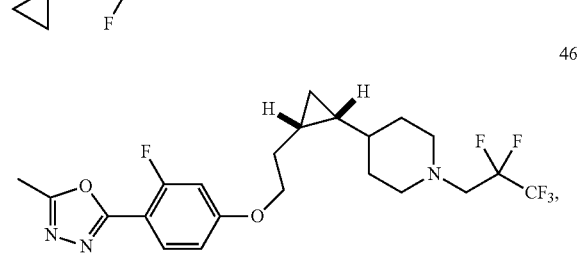
46
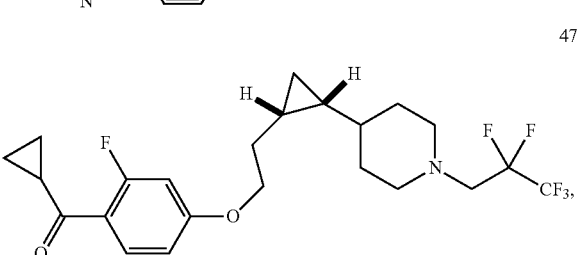
47
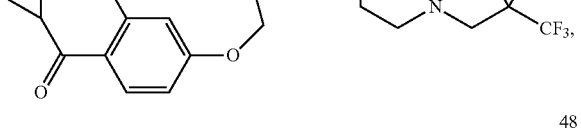
48
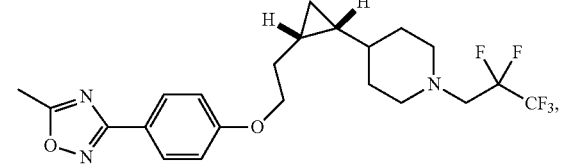
49
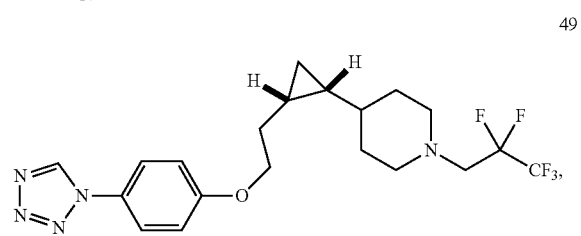
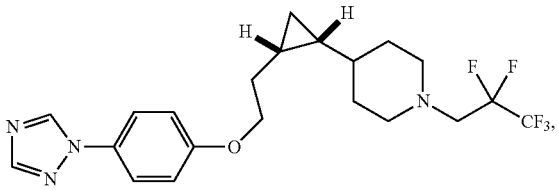
50
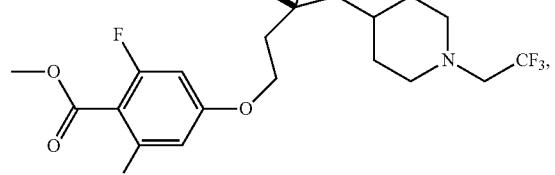
51
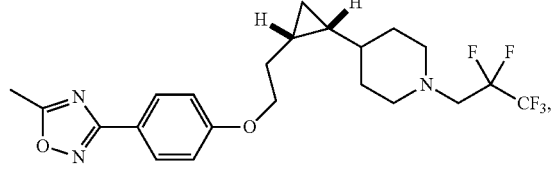
52
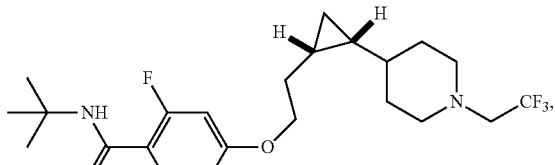
53
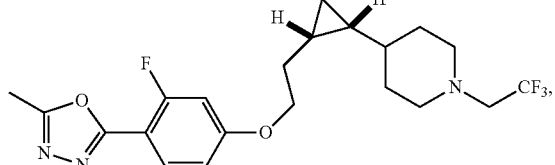
54
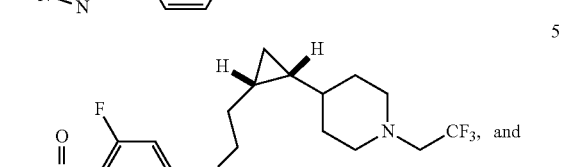
55
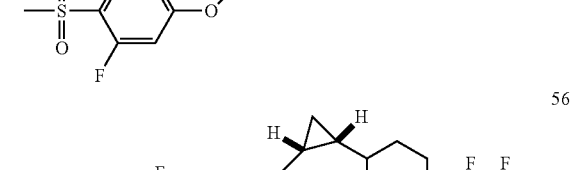
56
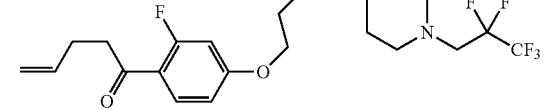
or a pharmaceutically acceptable salt thereof.
15. A pharmaceutical composition comprising the compound of claim 1, or a pharmaceutically acceptable salt thereof, and a pharmaceutically acceptable carrier.

16. A compound which is:
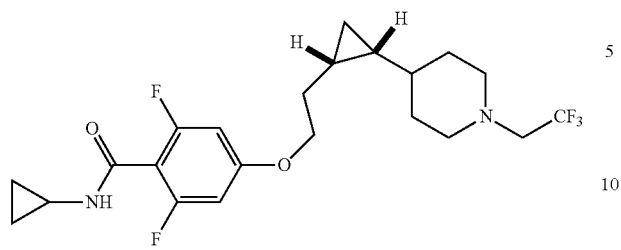
or a pharmaceutically acceptable salt thereof.
17. A compound which is:
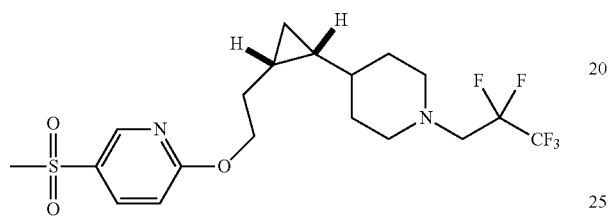
or a pharmaceutically acceptable salt thereof.
18. A method for treating a condition selected from the group consisting of diabetes and obesity comprising administering to an individual the pharmaceutical composition of claim 15.
* * * * *